United States Patent
Blakely et al.

(10) Patent No.: US 7,531,713 B2
(45) Date of Patent: *May 12, 2009

(54) ASSAY FOR TOXIN INDUCED NEURONAL DEGENERATION AND VIABILITY IN C. ELEGANS

(75) Inventors: Randy D. Blakely, Brentwood, TN (US); Richard Nass, Nashville, TN (US); David Miller, Brentwood, TN (US)

(73) Assignee: Vanderbilt University, Nashville, TN (US)

( * ) Notice: Subject to any disclaimer, the term of this patent is extended or adjusted under 35 U.S.C. 154(b) by 362 days.

This patent is subject to a terminal disclaimer.

(21) Appl. No.: 11/029,895

(22) Filed: Jan. 5, 2005

(65) Prior Publication Data

US 2005/0160482 A1    Jul. 21, 2005

Related U.S. Application Data

(63) Continuation of application No. 09/888,233, filed on Jun. 22, 2001, now Pat. No. 6,894,205.

(51) Int. Cl.
G01N 33/00 (2006.01)
C12N 15/00 (2006.01)
C12N 15/09 (2006.01)

(52) U.S. Cl. .............................. 800/3; 435/455; 800/21
(58) Field of Classification Search ..................... 800/3, 800/13, 21; 435/455
See application file for complete search history.

(56) References Cited

U.S. PATENT DOCUMENTS

| 6,146,826 | A | 11/2000 | Chalfie et al. | .................. 435/6 |
| 6,172,188 | B1 | 1/2001 | Thastrup et al. | ............. 530/350 |
| 6,518,035 | B1 * | 2/2003 | Ashby et al. | .................. 435/18 |
| 6,894,205 | B2 * | 5/2005 | Blakely et al. | ................. 800/3 |

OTHER PUBLICATIONS

Nass et al. Society for Neuroscience Abstracts, 2000, 26(1-2): 1536, Abstract No. 572.7.*
Nass et al., Pharmacology and Regulation of the *C elegans* Dopamine Transporter, 1999, International *C. elegans* Meeting 619, Abstract.*
Song et al., 1998, J. of Neuroscience, vol. 19, pp. 4119-4132.*
Nass et al., PNAS, 2002, vol. 99 No. 5, pp. 3264-3269.*
Baffi et al., "Differential expression of tyrosine hydroxylase in catecholaminergic neurons of neonatal wild-type and Nurr1-deficient mice," *Neuroscience*, 93(2):631-642, 1999.

Barker and Blakely, "Norepinephrine and Serotonin transporters. Molecular targets of antidepressant drugs," In *Psychopharmacology: The Fourth Generation of Progress* (Ed. By Bloom and Kupfer), Chapter 28: 321-333, 1995.
Braungart et al., "MPTP-based test system for Parkinson's disease in *C. elegans*," 2001 International Worm Meeting Abstract 128.
Chalfie et al., "Green fluorescent protein as a marker for gene expression," *Science*, 263:802-805, 1994.
Choi et al., "Two distinct mechanisms are involved in 6-hydroxydopamine- and $MPP_{30}$ -induced dopaminergic neuronal cell death: role of caspases, ROS, and JNK," *J. Neurosci. Res.*, 57:86-94, 1999.
Fradkov et al., "A novel fluorescent protein from Discosoma coral and its mutants possesses a unique far-red fluorescence," *FEBS Lett*, 479:127-130, 2000.
Heim et al., "Wavelength mutations and posttranslational autoxidation of green fluorescent protein," *Proc. Natl. Acad. Sci., USA*, 91:12501-12504, 1994.
Jayanthi et al., "The *Caenorhabditis elegans* gene T23G5.5 encodes and antidepressant- and cocaine-sensitive dopamine transporter," *Mol. Pharmacology*, 54:601-609, 1998.
Kitayama et al., "Parkinsonism-inducing neurotoxin MPP+: uptake and toxicity in nonneuronal COS cells expressing dopamine transporter cDNA," *Ann. Neurol.*, 32(1):109-111, 1992.
Koelle et al., "*C. elegans* gene knockout protocol," Article found at http://info.med.yale.edu/mbb/koelle/protocols_Gene_knockouts. html. Updated Sep. 18, 2000.
Link et al., "A transgenic *C. elegans* model for Parkinson3 s disease," 2001 International Worm Meeting Abstract 879.
Lotharius et al., "Distinct mechanisms underlie neurotoxin-mediated cell death in cultured dopaminergic neurons," *J. Neuroscience*, 19(4):1284-1293, 1999.
Miller et al., "Two-color GFP expression for *C. elegans*," *Biotechniques*, 26:914-921, 1999.
Miller et al., "Dopamine transporters and neuronal injury," *Trends Pharm. Sci.*, 20:424-429, 1999.
Nass et al., "Neurotoxin-induced degeneration of dopamine neurons in *Caenorhabditis elegans*," PNAS, 99(5):3264-3269, 2002.

* cited by examiner

*Primary Examiner*—Valarie Bertoglio
*Assistant Examiner*—David Montanari
(74) *Attorney, Agent, or Firm*—Fulbright & Jaworski, LLP

(57) ABSTRACT

Provided are in vivo screening methods to detect and identify substances that affect neuronal viability, and/or prevent neurodegeneration, and/or confer neuroprotective effects The screening methods utilize recombinant *C. elegans* expressing a detectable marker in neuronal sub-groups and the use of neurotoxins specific to specific neuronal cells. Also provided are methods for identifying modulators of neurotransmitter transporters such as the dopamine transporter. Therefore, the invention provides methods for identifying substances that can be used in the prevention and therapy of neurodegenerative diseases.

25 Claims, 8 Drawing Sheets

SEQUENCE LISTING

<160> NUMBER OF SEQ ID NOS: 4

<210> SEQ ID NO 1
<211> LENGTH: 719
<212> TYPE: DNA
<213> ORGANISM: C. ELEGANS

<400> SEQUENCE: 1

```
ccatgaaatg gaacttgaat ccagttttca ctaaaacgac ctcatacact ttctctcgta      60
tcctcaaaat atctatgaca ttatcattag cttcgctagt ttcatttctt tcaaatatta     120
```

```
tgcattctta aattccgata cccgcgtgca aaagtgctct attgagcaac tttgggatca      180
tatgtacaca ccaatgccct tttcccaaat ctttcctgt ccttttctct aaaaacaata       240
aatccatgcc tattccagta tgaccccttt gaagcagata taatcgcaca acatataca       300 catagctcgg ataaatgtag aaaaagaaga aaagaagtat aagtagatag atgctttccg      360
gcaattatcc accgcaccgt agtcttcacc aactgagact gcgtcgttag gagacgccga      420
catgattcag aagcagaatt tggaagaaaa acgacgatga tattgaggct ggcacacata      480
caccggaata ttcgacatgc caccacatct agattccaag gcaatctcta cctcttccca      540
ttctttcggt ttttttgttc tgacaagaaa agtggatagc tacgggctca atgagctgat      600
tttattttta aatatcttaa aactatacta gattcatgtg ttttcaggtc catattccaa      660
attagtcgaa aagctgatcc cgctacggtt tactcgaatc tcaacaattt ttagccatg       719
```

<210> SEQ ID NO 2
<211> LENGTH: 10851
<212> TYPE: DNA
<213> ORGANISM: Homo sapiens
<220> FEATURE:
<221> NAME/KEY: modified_base
<222> LOCATION: (9514)..(9636)
<223> OTHER INFORMATION: N = A, C, T/U or G

<400> SEQUENCE: 2

```
aaaggcgaga ctgaatatgt ttaatagaga catgacagat atttttttaaa agacacgaat     60 ccaaattcta gagatgaaaa ccacaatgtc tcagatgcaa aatgcactgg ttgagaggag     120
gggtggattc aacatctcag aagaaaagga tacatgaact tgaagacata gatggcagtg    180
caaactgttc aaaatgaaat aaagaaaaaa gacaaaaaaa tgaaccaagc atcagagaac    240
tgtgggactt caagccacct aatatgcaag ccataggaat cctcaaaaca gatcatgtct    300
aaacaatgtc attttatgat agcatcagtt caccaaaagg acaaatgttt atgtacctaa    360
taacatagct tcataatgaa ttcggcaaaa actgatagaa ctgcaaggag acatagagca    420
gttcacacaa ttatacttgg agatttcaat acctcttcc caatagttga tagaacagat     480
acacagaaac ttttaaggat acagaagact tcaaaaacag tacgaactaa catgacctat    540
ttgatattta acaataatt catccaataa tagcagagtg cacattcttt tcaaatgcat     600
gtgaaaagct taccaagatc gaccacagtc cagaccataa aattccctt agggattcag     660 gtcatgtaaa gcaagttctc caacaaagag gcaaataaat ttgataccaa atgaaaaat    720 acatttggca aaaaataaag aagcatatcc agacaatctt ctaatatttg gaaactaatc    780
acatatctaa ataacaatgg gtcaaagagg acatcaaaag ggaaatcaga aaatattttg    840
aactgaatga aaacaaaaca acatatcaaa ccttttggaa tttggctaaa tcagaactta    900
gaagaaaatc tagacatgaa gcctgcctca gaaggaata atgatgaaaa attgatggca     960
gcctccaccc gaagaaatcc catgcgggac tttggaagaa attgaaaagt tgattccaaa   1020
attcatatga aaaagcacag gaccgagaat atgcaaaaca actttgaaaa tgaacaaagt    1080
tgtctgactt acattacctg atttaaaaat gtattacaaa aggaccataa tgaagatagt   1140
gccattttaa tctcctcagg ctgccacaac aaaatacacc agatttgggg gcttaacagc    1200
agacatttgt ttctcacagt tctggagact ggaaatccaa catcaaggca gctgattcag    1260
ttcctggtga ggcctctctt cctggcttgc agatggccgc cttcttactc tatcttcaca    1320
tggcagaaag taaaatggag agagcttcct cttcttataa ggccacagtc ctcctgggtt    1380
```

```
atgacccccac ccttacaatt taatttaacc taatcacctc ctaaagtccc tatcctccag    1440
ataaagtcac cttgcggggg ttatggcttt aacctatgaa tttgggggta aacaattcag    1500
tccacagcaa gtgtggtatt agcatcaaaa tggattaaca gatcataaaa cagggagccc    1560
agaaataaac ccacacacat acatacaact gacttttcaa caaaggtgca aaagcaactc    1620
agcagaacac tgaacaactg gctcttcgga ggtaaagtgg tgaacttcaa ttggtgtctt    1680
acaccaagct agtttaaaaa tgcattctat gtgtaaatat gcaatctata attttaaaaa    1740
gtttagagga aaacttagga gaaaatcttg atgatcatga atttggtaaa gatttcttaa    1800
atacaacact aaaagcagga tttgtgaaag aaaaatggat aaattcgact tcatcaaaat    1860
taataactct tctctgaaag aatctattaa gagaatgaaa agacagtcca agactgggaa    1920
aaatatttgc aaagtaccca tctgataagg gactggtatc cagaatagta aagaactctc    1980
aaagctcaat taaacaaccc aaaggtgcaa aagatttgaa cagacactta acacgaagtg    2040
gcactgatgc agctaacaca tgagaaattg ttcaaagatc acgctcatta gagcagtata    2100
ggagatatta ctgtaaacat attaggatgt ctaaaattta aaagactgac catactaagt    2160
attcattaga atatgaagta actaaaatta tcatacactg ttcatggaaa tataaaatga    2220
tacaactact ttgcaaaaga atttaacagt ttttaaaaaa atagttaaac atatatctta    2280
ccaaatgacc cagccattcc acaactaagt acttcttacc tacccaaag taatgagagc    2340 ctatgttcaa agacttgcac acaaatgttc atagtagctt tatttgtaac agccagatgt    2400
ccatcaatag gcagatggaa aagccaagta catcatatcc catccaca caatggatac    2460 tacaaataac taaaagggaa ttaactgccg atgcaatgat gtggattctt ctcaaatatg    2520
ctgaatgcaa aagaacagac ccagaaaaca gtacttactg tataattcta tttatataaa    2580
attctattaa aaacacattg ttctgtaatc atagaaaaca aatcattcca ccatttgggg    2640
aggccaaggc gagcttatca cttgaggttg ggagttcaag accagcctgg ccaacatagt    2700
gaaaccctgt ttctactaaa aatacaaaaa ttagctgggt gtggtggcgg gcatctgtaa    2760
tcccagctac ttgggaggct gaggcaggag aattgcttga acttgaggag gcaaaggctg    2820
cagtgagctg agatcgtgcc actgcactcc agcctaggtg acagagtgag actccgtctc    2880
acaaaaagaa aaaaaaaaag agcaaatcag tggttgcctg gggatgggaa gaggtaaaga    2940
gacacagaca gagggaagtc agcgagggag gagcaccgcc atcatcttct gtgtgatcgc    3000
gttgccatga ccccatcagt cactcaccaa atcgtacact tggaatattg catatccatt    3060
acacctcagc aaggctgttt ttaaaaagac acaaatgccg agataattac agaaaaaaag    3120
tccaattagt tttgttagga tggtggaatc atgaaaggca tctcctaggt cctccaatgt    3180
tgttcttttt caagattctt ttggctactc taggtcaccc acatctccaa acacatttta    3240
gaaccagctg gttaatttct tcaaaaaagc aagttagaat tttgattgag attgcattga    3300
atctgtatgt caatttatga agaactgaca tctcattaat attgagcctt tcagtcataa    3360
acatacacac tcctctgctt gtctagactt caaaagtttc tcacagcaat ggattctagg    3420
ttttcggtgc acaagtctcg gatacgttta tccccaagca ttttgtttcg gatgctattg    3480
taagtgaaat tattttaggt tttattttag aattgtttgc tgccagtaca tagaaataca    3540
attggttttc atcagatccc atggccttgc taaattcatt tataaattct agtagttttt    3600
tttgtaaatt cctcaagatt ttctacaaac atgaaatcta ccaagaaaaa tcttgtcatc    3660
aatatttcaa ttttttttgaa gcctcctgct ctgtagccag accattcgcc actgcctatg    3720
actacattta gggccatcct ctggccatcc ctccttggct agatgatgaa cctgatgcat    3780
```

-continued

```
ggtttgaata tgtgcccact gggaagcttt ctttcactgg tctttcacag aaggccatga    3840
tgacacagcc tttcactttc tggtgggggc agtgtgctgt gtatagacac atgtaatcca    3900
ggccccaacg catgcatttt ctccgttcaa tgtcataaga aactctcatg tagccagagg    3960
tctgggttaa ggaagcggtc tccatgcagc aagaatgggt gcttgttcat ggaacttacc    4020
gcgcttccag acttgctcaa gccttgtgtc gtaaacattc cactgaggac ggcaggatgc    4080
tgtatacaca acctctgtgg gtccgataac aaatagcttc tgctgggccg ctcagcttct    4140
atggtaacag agctccctga gtttctgcta tggctcaggg ctgctcttac tcaaaaggag    4200
aggacgtatt ttcaggagag cgttcagctc ttaattcaac tgttattttc tgcgctgcct    4260
acaacatctc cgtctgccac agaccctcca attcccactg gttctgccag atcagtgttc    4320
tcaaagtgtg gttcctgggc cagcagtgtc agtgtcacct gagaactttc tagaaacgca    4380
ggtcctcagg tcccacctca gacctactga acctgcgtct ctaaggatgg agcgaggtga    4440
tctgtgcctc ctatgcatgt aaaggtttat gtaggtgact gtgatgccag ctaaagtcgg    4500
agaacaacac cagattgtgt ggcctcctgg ggcagcagtt tgcccatcca gaccagcagc    4560
agaatctttc ttactctggg ccctactcaa aaccaaacgc tttatgaaga acacaaaaca    4620
ggccagagaa gcatccccga gtgtcttgca cctcacttg caaatcggaa gagcctcacc    4680
aggtatgata cttctttctt agtggtagtc ttgcttgcca gagacagcgt gttttctttc    4740
attttggata tatatttga ccaatcagac caatggaccc acagaaagtt caccaaggtg    4800
gcaggttttg aaaatgtgtt attttctctt tcaatttta gcaagcacgt gtcttaccaa    4860
ggcatcttgg cattttcat ttttgctcc ccaggttgat tcagcctgat gtcatcagtg    4920
tggcagacca ctgtgacatg ctgtgcagtg gcaagaccat caagatgtct gtgactaaaa    4980
ccagcagtga gccggaaaat gatacagctc tgagagaaga cattggaagt gtactgctgt    5040
ccctgccatg cgagaggaaa ctatcttcct cctgaggtgg ccccggggga gggcacaggg    5100
gtgcagcagt gagcagggcc tcctgcctgg agccagcgcc ttccatcatt ctcagaacct    5160
ggacagacaa ggtctgggat ctgacctccc acacccctgg acaaaagcca ctcctgccta    5220
ctggtcccct caccctggcc ctccccaagc cccctacccc cagggccttc ccagcaccag    5280
tgagagtcag ggtctttaaa gtctgagctg ggctccctgg gacttcctct gaaagcacac    5340
aggacaccct caatatagta aatacgcagg caggtaaatg actgtcatct cactgccact    5400
gtccttgtcc cctctcagat acagcactca tggggggagc atccacgctg tcttccaaat    5460
caggcgagac acggcgcaac atccagcact gagggcctcc caggaggcag cacccaagga    5520 ggggggggacc cgtggggcaa ggttgctttg gagacagcag tcagtggcca ggggctcctt    5580
gtgggctctg cagctgcggt cccagccagt ggggagaggt gccgagcatg gcaggaagt    5640 gcagaggcag gggggctcca cctgcctgca cccaacgccc tgagcccaca gcagccatag    5700
cagcaaccac aatgataata aagccgactt ggcatttagg gcaaagttcc aagcatgcaa    5760
aggtcggccg tttgatcagg tctgatcagc tcataaccac actgcttcta cctgcacagt    5820
tcacggagca ttcctgttgt gggaggatgg agacccatgg gtctggcagc tgcgctttct    5880
ctgtgtcatc catgagccca actcccgcag ttagtttgtt cttagagcac ccaaagctcc    5940
tttatcctaa ttcatgtggt tggaagtcgg ggttgaggca ggggtggagg aatgctcttt    6000
gtcttggcag agtgcaggtt acatgcgtgt gatcactcag tggcccctcc tgagtgtggc    6060
aggtgcattc tctgtgtgct actggtcagt aaggatgtgg ctgcctggat ctgtgtgacc    6120
```

```
tctagtccct gcaccttcct gcctgtaccc tgttagcttt gggtcacaat tctgcgctcc    6180
tgcagcgctt gcaatccctt cccaaacgct gtttgcctgt gtgttgtttt gtttcgagac    6240
agggtctcat cctgtggccc atggcgcaat ctcagctcac tacaacctcc acctcccagc    6300
ttcaagctat tctcccacct ctgcctccca gtagctggga actacaggtg tgggccacca    6360
tgcctggcta attttttttt tcaaagtcag ggttttgcca tgtggcccag gctggtctca    6420
aactcctggc tcaagagat cctccttcct cggcctccca gagtgctggg attacaagcg    6480
tgagccctca ctcctggcct gtgtattttt aatatacctg aacatccatt ctctctgtgt    6540
gttttattta acagcctccc ttagtcacct gcaaagtctt ttccttggga gactgtttcc    6600
tcaaccctgc tgctctgggg ccaagccctg gctcactcct ttttattgaa acctgtgcca    6660
tggagataat aggggtagag agatcccttc tgtggcagcc actgacacac tacagcttcg    6720
aggtggcaca tccccctctc ctgaagtccc ctcacctccc tggcgatgaa gtcccacccc    6780
tgatgggagg tggtgtcagg aggccttcag gtggtcaggc caggagggct ccaccctgag    6840
gaatgggacc agtgccctca taaaacagac cccggagagc tctccccagc ccctagcgtg    6900
gggagataca gggagagaac tgtctgcaac cccgaagcgg ccctcaccag acacagagtc    6960
ggccaggcct tggcctcggg acaccggaac cgttagaact gaaggcttct gtgtgagccc    7020
ccaggctgtg gagttttttg tcatggcagc cccaggggt cactaggctc ccacttgatt    7080
ccaactcagc gtgaagtcac agccctgagt gccttctgcc tgggtgccag ccccggagcc    7140
ggggagcggg ggagcggggg gcgggagggg gagtggtggt gtgcgggag tgcggggcgg    7200 gcgcagggg tggggcaccg cgctgcgggc gggtactgcg gagtcaggca ccaagggtcc    7260
ctgcctccct cactgctgag cgcgggctgc aggctggaat ggctggagag ccccagggct    7320
cgcctggacg cccagggcag ggtgctcacg ggagcatcga gggtacacgg ggaggaacgc    7380
cggggttcgg gcgacccctag gggcgacgca cagagctggg cgcggccact cacctcggtg    7440
ccttctaagg acctggacat cctgggcctt ggcggcctgg gggctccatt cctccgcgcg    7500
ctgaatggaa gaaatcccgc ccgggcatct cggaaggaaa gcctcggagt ccattcggca    7560
ctggagccgg ataccaaccg ccaggctttc caggcccgtc ccgggaaatg ttttcttagg    7620
cgagtgcgag gcgggccctt cggttccgat gcaggcgcaa tagatgccgg caaggcgggg    7680
ataggctagg ggacctcggt cgcctcgagg tcgcggagac cccaaggcca cggaaggacc    7740
cgcgtctccg cagcccgcac gccgggaagc gtgcagagtc ctcggcgggg tcccgagccc    7800
gctggtcaga gcgtggagcg gcggggtggg agggacgtgg tccccagagc gcggggccac    7860 cgtagggggcc cctgatgggg agggagggaa gggtcggccc gacggggtcc cagcagttcc    7920
ccgcgcgcag ccgctcggct ccctcccgt ccagctggga gccgccagcc ctgggcgtcc    7980
gaagatagcg ggtgcccggg gcagccccca ggggtgcggg cgagggcgca ggccggccc    8040 agacagttcc cgcgtggaag gcgcccgtct agatccgcga cgtctcggac ccccaggccc    8100
ccgcaccccg tgtccgaggc tccggacgc gcaggacagt ggagccgtgg ccgccgcttg    8160
ctcccagcca tctgcgtccg ggaagcgggg cggggggcgc ggcccgggga ggtgaggagg    8220
aggagccagg acgcgagggc gaccccgtcc gcgggagggc gggggcgggc ggaccctgtc    8280
tactggataa gacccgaggc cgaagctgag accgcccagc gctgcggagc gggaggggag    8340
cttcgcggaa cgctctcggc gccaggactc gcgtgcaaag cccaggcccg gcggccagg    8400 tgaggccagc gtcgctcgcg gcatcggggc gccccgctcc ttccgcagac cccgaagtgg    8460
ggcgcagggg cgggggccgg gggccgggca cagtctgggg tccccgcgtc ccgcagaccg    8520
```

```
cgccgtctcc aaagtcgcca acagtcgcgg gtgccgagcg ccccccgata gcgccacatg    8580
ggaccctgag gccgtccgag gcgcgaggag ggtgcagggc tgcccctggc cccgctccaa    8640
gctcagaacc gggtgggcac ctggtgcagt caccggctta agggacgcgt gggtgtctat    8700
ggctgtgact cgggggtctg gtttcttctc gtggaattaa cctactaagg gtgcggcgca    8760
tcccagatcc gatcggaatg ggttttgtac accgccgctc catctcgcgg gggctttgtc    8820
tgtgttgggg gtggtggcgg gcgccggctg cgcgctggtg ctctgggcaa ggcggggaag    8880
ccgggcgagg actcgccagg cagcgccgct tcttgttctg ggcgcggtga ggaaggacgc    8940
tttctaacgg gccacatttt gctgtgtaga ccaaaatcgc ctctgaggcc ccgcgttcag    9000
gagcggggtc aggtggcccc agggcggcgg cggcttgccg gaaactcgcg agctccgcac    9060
ccgacgccct ctcccaacgc ggcctcctgc tcgcgccgcg gaacccttc gtcgggtgtt     9120 ttacccaccg gaggggtcgt gccggttgag gttgtcaccg ggtgcgtggc atagctcgtg    9180
atagctcatg ggtgaggttt tgtgcaaact tggatgcagg gaaagttgcc tgttagagcc    9240
tccacctgcg acctgcttca gtcgttgtgt gtgtgtgcgc acctgtgtga gtgtgagtgt    9300
gtatgtgtgt aagtgtatgt gctcgcctgt gtgtgtgtga gtgtgtatgt gtgtttgtga    9360
gtctgtgtgt gtctgtgtgt ctgtgtgtgc gtgcgctcga ctgaaacacg ctgctgctgg    9420
atccaaatga cagaagtcgc cctggctggg gcggtgtaga cgctcctgct ctcctgctca    9480
gcgttgcagg ggggtttatg taccgtttgg acangattc ccgggttacc ctgctggccc     9540
aagaactaat tcccgcnang aaaccctgtc catcctccgc ccaactctct cacgcggggt    9600
ggtgccacct gccctaagtg gatgtggctt gtacanacac ttttgagga agcagttgtg     9660 atggttatgt ctaaactttc tttaacagtg gctgattttg ctttatataa attttgttct    9720
ttattaactg agtataaaca atacaagccc aggcttggtg gctcatgcct gtcatctcag    9780
cactttggga ggctgaggca ggaggatcgc ttgagaccag gagttcaaaa ccagccttgg    9840
caacaatagt cagaccctgt ctctacaaga aaacaacaac aacaacaaaa aaacacacac    9900
aaaaataact tagccggtgc tgtggtgcac acctgtagtc tcagctgctc aggaggctga    9960
ggtgcaagga tcacttgaac ctaggaggtt gaggcagtga gttgtaatca caactgtatt   10020
ccatcctggg tgacagagcg agacctcatg ttaaaaaaga aaaaaaaaag aaaaaagaat   10080
acagatgaac agtcatgaag acattattga atgctcttag aagattgtaa aattgctctc   10140
tggaagtgtg ggggaaggtg gaagtgatat ccatgcattg ttagtagaaa gccacgctag   10200
agctcacaca gccttgcact ttgataggag tggggagggg tgcagggaa ggaggagcaa    10260 accagagtgt ctgtcttgag gcctccatgg gccagtgccc cagccctgtg gtgagggctg   10320
gcattcccag ctcccgtgcc ccagctgtac catctccagg cgtgagaagc acccatcctt   10380
tcccagagga atgcccgtga atgcttcggg gtctgccatc cgcaacaggt atgtccctag   10440
ccctggctga tgaattgttg cgttcctgtt gtgtgtttat ttttcatatt ggctgaagac   10500
caagagggaa gaagcacaga attctcaact cccagtgtgc ccatgagtaa gagcaaatgc   10560
tccgtgggac tcatgtcttc cgtggtggcc ccggctaagg agcccaatgc cgtgggcccg   10620
aaggaggtgg agctcatcct tgtcaaggag cagaacggag tgcagttcac cagttccacc   10680
ttcaccaacc cgcggcagag ccccgtggag gcccaggatc gggagacctg gggcaagaag   10740
atcgatttct cctgtccgtc attggctttg ctgtggacct ggccaacgtc tggcggttcc   10800
cctacctgtg ctacaaaaat ggtggcggta atcccatctc agcttccctg a            10851
```

```
<210> SEQ ID NO 3
<211> LENGTH: 12
<212> TYPE: PRT
<213> ORGANISM: Artificial Sequence
<220> FEATURE:
<221> NAME/KEY: MOD_RES
<222> LOCATION: (4)..(5)
<223> OTHER INFORMATION: Xaa = anything
<220> FEATURE:
<223> OTHER INFORMATION: Description of Artificial Sequence:  Synthetic
      Peptide

<400> SEQUENCE: 3

Trp Lys Gly Xaa Xaa Thr Ser Gly Lys Val Val Trp
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 4

Ala Tyr Phe Ser Ser Tyr Asn Asp Lys Phe
 1               5                  10
```

ASSAY FOR TOXIN INDUCED NEURONAL DEGENERATION AND VIABILITY IN C. ELEGANS

The present application is a continuation of U.S. application Ser. No. 09/888,233, filed Jun. 22, 2001, now U.S. Pat. No. 6,894,205.

This invention was made with government support under grant number DK58212 awarded by the National Institutes of Health. The government has certain rights in the invention.

BACKGROUND OF THE INVENTION

1. Field of the Invention

The present invention relates generally to the fields of neurobiology and neurodegenerative diseases. More particularly, it concerns the development of screening methods to detect and identify candidate molecules that confer neuroprotective effects following toxin-induced neuronal damage. The invention describes in vivo screening protocols using a recombinant C. elegans that expresses a detectable marker in sub-groups of neurons, such as, dopaminergic neurons.

2. Description of Related Art

Neurodegenerative diseases, strokes and neuronal injuries caused by trauma are typically characterized by neuronal cell death of groups of neurons. Among these neurological disorders, neurodegenerative diseases such as Alzheimer's, Parkinson's, Huntington's, amyotrophic lateral sclerosis, etc., afflict a large percentage of the population. For example, Alzheimer's disease alone afflicts about 4 million people in the United States, primarily the elderly, and is characterized by progressive memory loss, disorientation, depression and eventual loss of other body functions. Amyotrophic lateral sclerosis afflicts about 30,000 Americans, typically begins after age 40 and results in progressive weakness and paralysis. Huntington's Disease afflicts an estimated 25,000 patients in the United States, usually begins between the ages of 30 and 50 and includes violent, involuntary movements. Parkinson's Disease (PD) affects over 1 million people in the United States, and also usually begins on or after age 50. PD is another progressive disorder of the central nervous system and is characterized by a decrease in spontaneous movements, gait difficulty, postural instability, rigidity and tremor due to the degeneration of dopaminergic neurons.

In spite of great effort, little is known about the molecular basis of these disorders. Although the use of vertebrate and tissue culture systems continue to provide valuable insight into the pathology of the neurodegeneration, the molecular determinants involved in the etiology of these diseases remain elusive. As a result, there is an acute deficiency of effective therapeutic agents to treat these neurodegenerative disorders.

Although several drugs currently are being used for treatment of these diseases, none of these drugs offer complete cure or reversal of these disorders. In fact, most drugs only temporarily relieve some of the symptoms associated with the disease and do not prevent further degeneration of neurons. Hence, these disorders have been termed as progressive neurological disorders. Thus, the main goal of researchers in this field is to identify agents that will provide preventive as well as therapeutic relief for such diseases. At present, there is no effective high-throughput method to identify molecules with neuroprotective abilities in vivo.

SUMMARY OF THE INVENTION

The present invention overcomes deficiencies in the art and provides effective screening methods to identify agents that confer protective effects on neurons. The subject invention is based on a screening assay developed using the microscopic transparent roundworm Caenorhabditis elegans (C. elegans), which is a particularly useful model for studying neurodegeneration because it allows observation of changes in cells within the living worm over the time-period that it takes to develop from a single-cell zygote to a mature adult. These kinds of observations are extremely difficult in other animals and impossible in humans. As the genetics of C. elegans are well known, and as the entire genomic sequence has been mapped, the C. elegans based screening system of the invention provides a powerful screening/identifying tool.

Therefore, one embodiment of the invention provides a recombinant C. elegans that expresses a detectable marker in a dopamine neuronal. In one aspect, the detectable marker is further defined as a marker that can be visually detected. In a particular aspect the detectable marker is further defined as a marker that can be spectroscopically detected. Some examples of detectable markers include green fluorescent proteins, yellow fluorescent proteins, blue fluorescent proteins and red fluorescent proteins. Other spectral variants, mutational variants and derivatives of such fluorescent proteins are also contemplated. Fluorescent proteins are preferred as they permit in vivo visualization of cells of the live worm.

In another aspect the detectable marker is β-galactosidase. Use of a marker such as β-galactosidase is however limited as it does not permit the visualization of live worms. Methods for detecting the expression of β-galactosidase using the substrate X-Gal are known to the skilled artisan. In yet another aspect, the detectable marker is an antigenic polypeptide positioned under the control of a promoter which can then be detected by staining with a labeled antibody. Methods for detection using antibodies are well known in the art.

In one embodiment the detectable marker is under the control of a promoter. In specific embodiments the promoter is a tissue-specific promoter. In other specific embodiments, the tissue-specific promoter is a neuronal promoter. Some neuronal promoters contemplated as useful are promoters specific to dopamine neurons such as the dopamine transporter promoters and the tyrosine hydroxylase promoters. In one embodiment, the dopamine transporter promoter region comprises the CeDAT promoter region comprised in SEQ. ID. NO. 1.

Expression of the detectable marker driven by specific promoters allows for the selective expression of the marker in specific subsets of cells, such as in dopamine neurons, cholinergic motor neurons, etc. The skilled artisan will recognize that the present invention is not limited to the use of the promoters described above and that any other specific neuronal, or other tissue specific promoter may be used in the practice of this invention. The main goal is to obtain expression of a detectable marker in certain specific populations of cells.

The strains of C. elegans provided by the subject invention can also be used in methods of screening drugs and other agents to identify substances that can prevent or decrease neuronal degeneration. In some aspects the neuronal degeneration is induced by a neurotoxic agent. One of the C. elegans strain is designated RN200 and comprises a C. elegans in which the dopamine transporter promoter drives the expression of a green fluorescent protein in a dopamine neuron.

Therefore, the invention further provides methods for screening for substances that affect neuronal viability comprising: (a) providing a recombinant C. elegans that expresses a detectable marker in a neuronal cell; (b) exposing the *C. elegans* to a candidate substance; and (c) detecting a change in the expression of the marker relative to the expression of the marker before the exposing, wherein a change in the expression of the marker corresponds to a change in the viability of the neuron. The method may further comprise detecting the expression of the marker in the neuronal cell in the absence of the candidate substance. In one embodiment, the method further comprises the step of exposing the *C. elegans* to a known neurotoxin prior to step (b).

The candidate substance may be a substance that affects neuronal viability by either decreasing neuronal viability or by increasing neuronal viability. The screening is intended to identify both neuroprotective substances as well as neurotoxic substances.

Therefore, in some aspects, the substance is a neurotoxic substance. In specific aspects, the neurotoxic substance is 6-hydroxydopamine, 1-methyl-4-phenyl-1,2,3,6-tetrahydropyridine, or 5,7,di-hydroxy tryptamine. In other specific aspects, the neurotoxic substance is a generator of free radical species. In still other aspects, the substance is an environmental toxin. Examples of environmental toxins include pesticides, herbicides, air pollutants, water pollutants, industrial wastes. The term "pesticide" as used herein refers to any type of chemical compound which has lethal or sub-lethal effects on eukaryotic cells. Encompassed within "pesticide" are such compounds as insecticides, vermicides, mutagens, carcinogens, and any other compound useful for killing, mutating, or debilitating organisms such as insects. "Pesticides" include, but are not limited to polychlorinated hydrocarbons such as dichlorodiphenyltrichloroethane (DDT), dieldrin, aldrin, chlordane and lindane; organophosphorous compounds; carbamates; rotenone; and any other compound useful in the killing of pests.

In other aspects, the substance is a neuroprotective substance. In specific aspects, the neuroprotective substance is a dopamine transporter antagonist. In other specific aspects the dopamine transporter antagonist is a *C. elegans* specific dopamine transporter antagonist (Jayanthi et al., 1998). Some non-limiting examples of dopamine transporter antagonists contemplated include imipramine, ampetamines, and cocaine.

In yet other aspects, the neuroprotective substance is a free radical scavenger. In specific embodiments, free radical scavengers include ascorbic acid (vitamin C), vitamin E, melatonin, and carboxyfullerenes, as some non-limiting examples. It also is contemplated that the substance may be encoded by a polynucleotide. In one embodiment, it is contemplated that the polynucleotide encodes a dopamine transporter regulatory gene, or a gene that suppresses free radical generation. In other embodiments it is contemplated that the substance is a polypeptide. The polypeptide may encodes a dopamine transporter regulatory polypeptide, or a polypeptide that suppresses free radical generation.

In other embodiments, the substance is a naturally occurring product. In yet other embodiments, the substance can be a man-made chemical. Some examples of substances contemplated as useful include monoamine oxidase (MAO) inhibitors. MAO inhibitors have been recently used in clinical trials for limiting the progress of PD. MAO inhibitors include hydrazine derivatives such as phenelzine or isocarboxazid or non-hydrazine derivatives such as tranylcypromine, or pargyline.

Therefore it is contemplated that any synthetic compound, or natural product, including macromolecular entities such as polypeptides, polynucleotides, or lipids and also small entities such as neurotransmitters, ligands, hormones or elemental compounds may be used as candidate substances. The synthetic compounds or natural products further refer substances that are either part of a crude mixture or purified and isolated, or just naturally occurring.

Other aspects of the method further comprise: (a) exposing the *C. elegans* to a known neurotoxin; and (b) detecting a change in expression of the marker. The change in marker expression can be an increase in the marker or a decrease in the marker expression.

In one aspect, the detectable marker is further defined as a marker that can be visually detected. In another aspect, the detectable marker is further defined as a marker that can be spectroscopically detected. Some examples of detectable markers include green fluorescent proteins, yellow fluorescent proteins, blue fluorescent proteins and red fluorescent proteins. Other spectral variants, mutational variants and derivatives of such fluorescent proteins are also contemplated. Use of fluorescent proteins is a preferred embodiment as it allows the screening in live animals which represents the most intact physiology and permits high-throughput in vivo screening.

In another aspect the detectable marker is β-galactosidase. Methods for detecting the expression of β-galactosidase using the substrate X-Gal are known to the skilled artisan. In yet another aspect the detectable marker is an antigenic polypeptide positioned under the control of a promoter which can then be detected by staining with a labeled antibody. Methods for detection using antibodies are well known in the art.

In one embodiment the detectable marker is under the control of a promoter. In specific embodiments the promoter is a tissue-specific promoter. In other specific embodiments the tissue-specific promoter is a neuronal promoter. Some neuronal promoters contemplated as useful, are dopamine transporter promoters, tyrosine hydroxylase promoters (encoded by the cat-2 gene), the cha-1 promoter which is predominantly expressed in cholinergic neurons, the acr-2 promoter which is predominantly expressed in cholinergic motor neurons, the unc-30 promoter which is expressed by predominantly in GABA-ergic neurons, the unc-4 promoter which is expressed by A-class motomeurons. Expression of the detectable marker under specific promoters allows for the selective expression of the marker in specific subsets of cells, such as in dopamine neurons, cholinergic motor neurons, etc. The skilled artisan will recognize that the present invention is not limited to the use of the promoters described above and that any other specific neuronal, or other tissue specific promoter may be used in the practice of this invention. The main goal is to obtain expression of a detectable marker in certain specific populations of cells.

In one embodiment of the method, the neuronal cell comprises a dopaminergic neuron, a cholinergic neuron, a GABA-ergic neuron, a glycinergic neuron, a serotonergic neuron, a cholinergic motor neuron, a glutamatergic neuron, or a peptidergic neuron.

Other non-neuronal cellular populations also are contemplated for cell specific expression of a detectable marker and include, vulval cells, pharyngeal cells, and excretory cells, among others.

Additionally, provided are methods of screening for substances that can inhibit neuronal cell death comprising: (a) providing a recombinant *C. elegans* that expresses a detectable marker in a neuronal cell; (b) exposing the *C. elegans* to a known neurotoxin and a candidate substance; (c) detecting expression of the marker; and (d) comparing the expression of the marker to the expression of the marker in the absence of the candidate substance. In some embodiments of this method, the *C. elegans* is exposed to the neurotoxin prior to the candidate substance. In other embodiments of this method, the *C. elegans* is exposed to the candidate substance prior to the neurotoxin.

The invention also provides methods of screening candidate substances to identify a substance that can be used for prevention and/or therapy of neurodegenerative diseases comprising: (a) obtaining a recombinant *C. elegans* that expresses a detectable marker in a neuronal cell under the control of a neuronal-specific promoter; (b) exposing the *C. elegans* to a known neurotoxin and a candidate substance; (c) detecting expression of the marker; and (d) comparing the expression of the marker to the expression of the marker in the absence of the candidate substance. The *C. elegans* may be exposed to the neurotoxin prior to the candidate substance or alternatively prior to the neurotoxin.

Neurodegenerative diseases contemplated include non-limiting examples such as, Parkinson's disease, Alzheimer's disease, Huntington's disease, a transmissible spongiform encephalopathy, a familial amyloid polyneuropathy (FAP), a prion diseases, a Tauopathy, a Trinucleotide disease, amyotrophic lateral sclerosis (ALS) or multiple system atrophy.

The invention also provides methods of screening for substances that modulate dopamine transporter function comprising: (a) obtaining a recombinant *C. elegans* that expresses a detectable marker in a dopaminergic neuronal cell; (b) exposing the *C. elegans* to a candidate substance; (c) exposing the *C. elegans* to a neurotoxin that requires a dopamine transporter for intracellular access; and (d) detecting any change in the expression of the GFP after step c.

In one embodiment, the candidate substance modulates the expression of the dopamine transporter. Modulation can be at the level of transcription, translation, post-translational modifications, insertion into the neuronal membrane, etc.

In another embodiment of this method, the candidate substance blocks transport by the dopamine transporter. In other embodiments, the candidate substance increases transport by the dopamine transporter. In yet another embodiment, the candidate substance is a addictive substance. Non-limiting examples of such addictive substances include cocaine, amphetamines, or methylphenidate. In still another embodiment, the candidate substance is a modulator of regulatory pathways that control the dopamine transporter promoter.

In one aspect, the method can be used to identify substances that provide therapy for neurological diseases involving dopamine transporter function. Examples of neurological diseases involving dopamine transporter function include schizophrenia, addiction disorders, attention deficit hyperactivity disorder (ADHD), psychoses, Tourette's syndrome, or Parkinson's disease.

The invention also provides a method of screening for molecules that modulate presynaptic neuronal signaling comprising: (a) obtaining a recombinant *C. elegans* that expresses a detectable protein in a neuronal cell which is a knockout for a component of neuronal signaling; (b) obtaining a second recombinant *C. elegans* that expresses a detectable protein in a neuronal cell which is a mutant for a component of neuronal signaling; (c) comparing the differences in neuronal viability when exposed to a neurotoxic substance in the *C. elegans* of step a) with the *C. elegans* of step (b); and (d) identifying the genetic component of the mutation. In one embodiment the method further comprises isolating the genetic component of neuronal signaling. In specific aspects the component of neuronal signaling can be signaling molecules that control dopamine metabolism such as α-methyl-paratyrosine, reserpine, or tetrabenazine.

Further contemplated is a method for screening post-mortem human or other animal brains for substances that can cause neurotoxicity. For example, it is contemplated that one would screen for substances, from a post-mortem brain of a patient with a neurodegenerative disease, that cause neurotoxicity in *C. elegans* neurons using the screening methods of the present invention. It is contemplated that initially tissue/cellular extracts, fluids, and similar partially purified preparations will be screened. The substances may be then isolated and identified. It is envisioned that one can then develop diagnostic assays to diagnose a subject for the presence of such neurotoxic substances thereby allowing one to predict the possibility of a neurodegenerative disease.

As used in this specification, "a" or "an" mean one or more. As used in the instant claim(s), when used in conjunction with the word "comprising", the words "a" or "an" means one or more than one and the word "another" means at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 3A), CEP and ADE neurons and processes as revealed by confocal 3D reconstruction of GFP signal in the anterior end of animals transgenic for a PDAT1::GFP transcriptional reporter. (FIG. 3B), Schematic illustration of the neurons shown in FIG. 1A. (FIG. 3C), PDE neurons and processes as revealed by confocal 3D reconstruction of GFP signal in the posterior-lateral segment of animals transgenic for a PDAT1::GFP transcriptional reporter. (FIG. 3D), Schematic illustration of the neurons shown in FIG. 3A. In FIG. 3A and FIG. 3C, large full arrow designates cell bodies whereas other arrows point to processes of the appropriate cell body. Scale bar=~10 micrometers.

(FIG. 4A), Transgenic worms treated with vehicle (ascorbic acid) prior to visualization. (FIGS. 4B, 4C & 4D), Worms as in FIG. 4A but treated with 10 mM 6-OHDA for 1 hr prior to plating and visualized 72 hrs later via confocal microscopy-various stages of apparent degeneration are evident. (FIG. 4E), Transgenic worms with PDAT1::GFP reporter coinucbated with 6-OHDA and 10 mM amphetamine. (FIG. 4F), Transgenic worms with PDAT1::GFP reporter coincubated with 6-OHDA and 10 mM imipramine. Coinucbation with either amphetamine or imipramine prevents visible evidence of 6-OHDA toxicity, consistent with pharmacological blockade of DAT-1.

(FIG. 5A), Control reporter transgenic line exposed to vehicle. (FIG. 5B), Reporter transgenic line exposed to 50 mM 6-OHDA. (FIG. 5C), Reporter transgenic line produced in a dat-1 deleted strain, exposed to vehicle. Reporter expression is identical to that seen in transgenic with normal levels of DAT-1. (FIG. 5D), Reporter transgenic line produced in a dat-1 deleted strain, exposed to 6-OHDA. Notice a failure of toxin to effect loss of GFP signal. (FIG. 5E), Plot of neuronal sensitivity to 6-OHDA in wildtype (blue) or dat-1 mutant (red) lines as a function of time of exposure. Whereas the wildtype line shows a time dependent loss of CEP neurons, the dat-1 deletion strain is protected.

(FIG. 6A), ASI chemosensory neurons made transgenic for a PDAF-7::GFP reporter to reveal these cells and their processes. (FIG. 6B), Worms in FIG. 6A treated with 6-OHDA. Notice little or no effect of the toxin on these cells that lack DAT-1. (FIG. 6C), A transgenic line where PDAF7::DAT1:GFP translational fusion is expressed in the ASI neurons, brining DAT-protein to these cells. (FIG. 6D), Animals in C, exposed to 6-OHDA. Transfer of the DAT1 transporter to the ASI cells conferred 6-OHDA sensitivity illustrating that DAT-1 transfer may allow other cells to be ablated and screened for selective responses to neurotoxins

DESCRIPTION OF ILLUSTRATIVE EMBODIMENTS

Figure 1A:
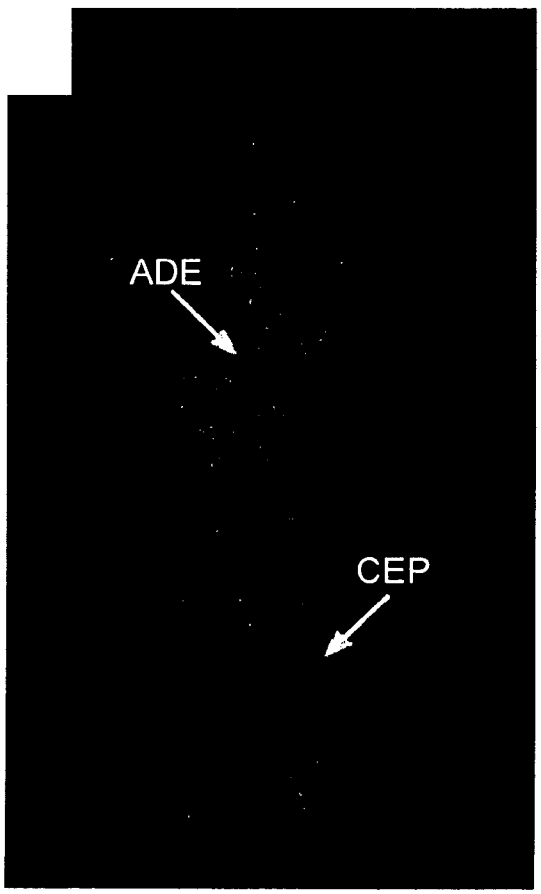
FIGS. 1A & 1B. A 3D confocal reconstruction (FIG. 1A) and differential interference contrast (DIC) image (FIG. 1B) of the six dopaminergic DA neurons located in the head of a hermaphrodite expressing green fluorescent protein (GFP) driven by the endogenous *C. elegans* dopamine transporter (CeDAT) promotor. Arrows identify the CEP and ADE DA neurons.

Neurodegenerative diseases such as Parkinson's disease (PD), transmissible spongiform encephalopathies (TSEs), Alzheimer's disease (AD), familial amyloid polyneuropathy (FAP) and Huntington's disease (HD), Prion diseases, etc., are characterized by degeneration and loss of neuronal cells. To date there has been no successful therapeutic agent that can provide reversal and/or prevention of degeneration.

Although vertebrate systems and tissue cultures are available for studying neurodegenerative conditions, they are relatively difficult to manipulate and the time course of such studies are generally very long. Because of the high conservation of genes and metabolic pathways between invertebrates and humans, as well as the availability of genetic strategies to identify novel proteins, protein interactions, and drug targets, genetic analysis using invertebrate model systems provides an enormous potential in deducing the factors involved in neuronal disease.

The present inventors have developed a novel screening method using the nematode *Caenorhabditis elegans* (*C. elegans*) for identifying substances that affect neuronal viability, neuronal cell-death, neuronal survival, and/or neuronal degeneration. *C. elegans* offers a system which is easy to manipulate genetically and in culture and numerous genes identified in *C. elegans* have mammalian and human counterparts with a high level of sequence homology.

The inventors have developed a recombinant *C. elegans* that selectively expresses a detectable marker in a set of neuronal cells, such as, in a dopaminergic neuronal cell population, in a cholinergic neuronal population, etc. Using such recombinant *C. elegans* that express detectable markers in one neuronal population, the inventors established conditions under which known cell-specific neurotoxins lead to a decrease or loss in the expression of the detectable marker. The inventors then developed a screening method whereby one can expose or contact the recombinant *C. elegans* with substances/candidate substances that can prevent/reduce damage by a neurotoxin, which is reflected by a decrease in loss of marker gene expression. For example, using 6-hydroxydopamine (6-OHDA), which is neurotoxic to dopaminergic (DA) neurons, the inventors demonstrated a decrease in a detectable marker gene, such as the green fluorescent protein (GFP), in worms selectively expressing such a detectable marker gene in dopaminergic neurons. The inventors then demonstrated that the decrease/loss of the detectable marker gene expression can be prevented or reduced by agents that block the dopamine transporter protein (DAT), which is responsible for transporting the 6-OHDA into DA neurons (see FIGS. 4A-F).

Thus, the present invention provides a powerful screening method whereby one can screen for agents that can prevent neuronal degeneration and/or neuronal loss. As neurodegenerative diseases are characterized by loss/degeneration of populations of neurons, this assay provides methods to identify substances that can be used as therapeutic agents. For example, in PD there is a selective degeneration of DA neurons in the substantia nigra. Thus, screening for agents that can prevent/decrease DA neuronal degeneration will provide putative therapeutic agents for therapy and prevention of PD. The invention is however not limited to PD and one may screen for substances that prevent the loss/degeneration of any set/subset/population of neurons. It is contemplated that the method will allow the identification of substances that can prevent neuronal damage by different types of neurotoxic agents, including environmental toxins, free radicals, drugs, chemicals. In addition, the method is contemplated to provide an assay for substances that affect neuronal viability. Therefore, it allows the detection of yet unknown neurotoxic agents as well as yet unknown neuroprotective agents.

Additionally, the system also provides a method for screening for substances that modulate DAT transporter function. The *C. elegans* DAT (CeDAT) is highly conserved to the vertebrate and human DAT protein. The DAT protein is the target of addictive substances such as the psychoactive stimulants including cocaine, methylphenidate, etc. Thus, substances identified by such a screening method can help identify therapeutics for addiction disorders. Additionally, the method also provides the ability to identify therapeutic agents for neurological disorders involving the DAT. This includes schizophrenia, attention deficit hyperactivity disorder, psychoses, Tourette's syndrome, etc.

In addition, the inventors contemplate methods to screen for modulators of presynaptic neuronal signaling using recombinant *C. elegans* expressing detectable markers in selective populations of neurons comprising monitoring responses to cell-specific toxins. These methods comprise comparing knockout strains of *C. elegans* that are deficient for a component of neuronal signaling, such as the DAT gene, with strains that have mutations in neuronal signaling pathways. Comparison of such strains can reveal genetic components involved in modulation of neuronal signaling by identifying the nature of the mutation and eventually the gene involved. For example, the mutation may be in other DAT regulatory genes, and/or in toxin suppressive genes, etc. Other methods contemplated include genetic methods whereby one can cross a knockout DAT *C. elegans* strain with a phenotypic DAT mutant *C. elegans* strain. If the cross rescues the knockout, this indicates that the mutation in the mutant strain is in a synaptic modulator or a toxin suppressor type gene, i.e., in a gene other than the DAT gene. One can then identify the mutation and isolate and identify the gene corresponding to the synaptic modulator or toxin suppressor. Although the discussion above describes DAT protein and its modulators as an example, this method is contemplated as useful for screening any molecule that can modulate neuronal signaling. Thus, one may screen for modulators of acetylcholine-mediated signaling, serotonin-mediated signaling, glutamate-mediated signaling, GABA-mediated signaling and the like.

A. Parkinson's Disease as a Model for Neurodegenerative Diseases

This section describes Parkinson's disease (PD) in detail, however, the general description applies to any neurodegenerative disorder. PD is a slowly progressive, neurodegenerative disorder characterized by the irreversible loss of over 80% of the nigrostriatal dopaminergic neurons. Although the pathogenesis of the disease appears to be multifactorial, correlative evidence supports the role of oxidative stress and mitochondrial dysfunction (Yahr and Bergmann, 1986). PD patients have reduced levels of mitochondrial complex I and glutathione activity, as well as increased levels of superoxide dismutase activity, lipid peroxidation, and iron in the substantia nigra (Yahr and Bergmann, 1986; Jenner, 1998). This evidence suggests that the generation of reactive oxygen species (ROS), such as the superoxide ion and hydrogen peroxide plays a significant role in dopamine (DA) neuronal death.

Current animal model systems of PD rely on inducing nigrostriatal damage in monkeys and rodents with the neurotoxins 6-hydroxydopamine (6-OHDA), 1-methyl-4-phenyl-1,2,3,6-tetrahydropyridine (MPTP), or 1-methyl-4-phenylpyridinium ion (MPP$^+$[the active metabolite of MPTP]) (Yahr and Bergmann, 1986). Toxin exposure causes DA neuronal death, and the animals exhibit many of the same symptoms as PD. The specificity of the toxin for the DA neurons lies in their affinity for the Na$^+$- and Cl$^-$-dependent dopamine transporter (DAT), a presynaptic membrane protein that terminates DAergic transmission by the active reuptake of DA into presynaptic neurons (Sachs and Jonsson, 1975; Glinka et al., 1997; Kitayama et al., 1992; Pifl et al., 1993; Javitch et al., 1985; Giros et al., 1996; Gainetdinov et al., 1998). Transfections of DATs into nonneuronal cells confer sensitivity to MPP$^+$, and 6-OHDA and MPP$^+$ toxicity can be blocked with DAT antagonist in vivo (Glinka et al., 1997; Kitayama et al., 1992; Pifl et al., 1993; Javitch et al., 1985).

Despite decades of research, the primary insults and mechanisms leading to the degeneration of the nigrostriatal DA neurons and the increase in production of ROS in PD is unknown. Non-human primates do not naturally develop PD, so these model systems are unavailable to study the etiology of the disease. Current animal and tissue culture systems are able to mimic some of the pathology and morphology of idiopathic PD. However, identifying the molecular determinants involved in PD without any a priori knowledge of the mechanism of the neurodegeneration is significantly hindered due to the lack of a definitive model system.

An approach to identifying the molecular determinants involved in PD without any prior knowledge of their function could be through forward genetics (Johnsen et al., 1997). In this classical method of genetic analysis, a well-defined phenotype is modified by mutagenizing the genomic DNA. The progeny that have the modified trait are further analyzed to determine the location of the altered loci (this is the opposite of reverse genetics in which the goal is to identify animals that have a specific gene mutated) (Johnsen et al., 1997). In order for forward genetics to be successful in studying DAergic neurodegeneration in an animal, either an aspect of the behavior should depend on normal DA neurotransmission, or the morphology of the DA neurons should be easily accessible. Furthermore, the organism should provide an efficient strategy to map and identify the mutated gene. Because of the above criteria, as well as their relatively long life-span and maintenance cost, mammals are not amenable for these studies.

*C. elegans* offers a powerful tool for dissecting the components involved in mammalian neurodegenerative disorders using forward genetics. *C. elegans* provides a model system due to numerous factors such as, the high conservation of the genome and metabolic pathways between nematodes and vertebrates; the ease of screening a large number of worms following mutagenesis for neural defects; and the ability to identify quickly the modified gene as the whole genome of *C. elegans* been sequenced. Thus, the *C. elegans* model allows for the rapid discovery of proteins involved in neuropathologies (*C. elegans* Sequencing Consortium, 1998).

The rapid rate of reproduction of *C. elegans* (approximately 3 days at 25° C.), and their relatively small size (approximately 1 mm), generates about 300 worms from a single hermaphrodite, allowing for rapid genetic screens involving large numbers of animals (Wood, 1988; Riddle et al., 1997). Yet other features of *C. elegans* that make them amenable for studies are the transparency of the worm, with virtually every cell identifiable under a light microscope. Furthermore, the entire 302-cell nervous system (approximately one-third of the total somatic cells of the hermaphrodite) has been mapped by serial 3-dimensional electron-microscopic reconstruction, allowing for the identification of virtually all synaptic connections (White et al., 1986).

Multicolor reporters, using spectral derivatives of the green fluorescent protein (GFP) from the jellyfish *Aequorea victoria*, also allow for the detailed visualization of cells, intracellular compartments, or protein localization in the living animal (Chalfie et al., 1994; Rongo et al., 1998; Miller et al., 1999b). Methods for generating transgenic animals (obtainable within 4 days) and production of gene knockouts averaging at about 1 week are also well developed (see Chapter 19, Mello and Fire, 1995). A significant advantage of the worm over vertebrate systems is that sexual reproduction can be achieved by self-fertilization and therefore is not disrupted by mutations that would otherwise perturb mating behavior.

The similarity between the worm and the mammalian nervous system indicates that the fundamental interactions that occur during DA neurotransmission and pathogenesis in vertebrates also occurs in *C. elegans*. Most of the molecular components known to be involved in DA signaling in mammals are also present in the nematode (Table 1) (Loer and Kenyon, 1993; Lints and Emmons, 1999; Duerr et al., 1999; Jayanthi et al., 1998; Sulston et al., 1992). Furthermore, analysis of *C. elegans* genome has revealed a high conservation of ion channels, neurotransmitter synthesis enzymes, including tyrosine hydroxylase (TH) and aromatic amino acid decarboxylase (AAAD); synaptic vesicle and presynaptic terminal proteins, including syntaxins, synaptotagmin, synaptobrevin; neurotransmitter receptors, including glutamate, acetylcholine, GABA, amine, and peptide; and neurotransmitter transporters, including acetylcholine (VchAT), the vesicular monoamine transporter (VMAT), GABA, glutamate (EAAT), serotonin (SERT), dopamine (DAT) (Table 1) (Bargmann, 1998).

TABLE 1

Genes of Catecholamine Biosynthesis, Metabolism, and Transport in *C. elegans*

| Gene | Protein | Reference |
|---|---|---|
| cat-4 | GTP Cyclohydrolase I | Loer and Kenyon, 1993 |
| cat-2 | Tyrosine Hydroxylase | Lints and Emmons, 1999 |
| bas-1 | Aromatic L-Amino Acid Decarboxylase | Loer and Kenyon, 1993 |
| cat-1 | Vesicular Monoamine Transporter | Duerr et al., 1999 |
| dat-1 | Dopamine Transporter | Jayanthi et al., 1998 |
| R13G10.2 | Monoamine Oxidase* | Sulston et al., 1992 |
| C48D5.1 | NHR, Nurr1 Homologue* | BLAST search at http://www.wormbase.org/perl/ace/elegans/searches/blast |

*Predicted gene product; NHR, nuclear hormone receptor

In addition, a mammalian nuclear hormone receptor, Nurr1, which is expressed in DA neurons and provides a measure of neuroprotection against MPTP toxicity, also has significant homology with the worm gene C48D5.1 (Baffi et al., 1999; Le et al., 1999; Castillo et al., 1998; www.wormbase.org/perl/ace/elegans/searches/blast). However to date, the cellular expression pattern of C48D5.1 has not been defined. An important distinction to make between the two nervous systems at the molecular level is the redundancy of the genomes, while vertebrates will often have several similar versions of a particular gene, *C. elegans* may have a single allele (Bargmann, 1998). This feature of the nematode genome provides an enormous advantage relative to vertebrate systems because it decreases the probability that a mutant effect will be masked by a genome redundancy. Finally, the genetic basis of cell death is highly conserved between the worm and vertebrates, and *C. elegans* provides an opportunity to explore genes involved in neuronal cell death (Hengartner, 1997).

The *C. elegans* hermaphrodite contains eight dopaminergic neurons which include six head DA neurons, four cephalic neurons (CEPs), and two anterior dereid neurons (ADEs), and two neurons which are located in posterior lateral positions, the posterior dereid neurons (PDEs) (Sulston et al., 1975). All of these neurons contain ciliated endings which terminate in sensory organs embedded in the cuticle that surrounds the animal. Laser ablation and genetic studies have revealed that these cells provide mechanosensory function during foraging and movement and may also modulate pharyngeal pumping and egg laying behaviors (Duerr et al., 1999; Sulston et al., 1975; Sawin et al., 2000; Lints and Emmons, 1999). The male contains another three pairs of DA-containing neurons in the tail that are involved in mating, as well as four additional DA-containing socket cells of the mating spicules (Loer and Kenyon, 1993; Lints and Emmons, 1999; Sulston et al., 1975; Sulston and Horvitz, 1977; Liu and Sternberg, 1995).

B. Detectable Markers

The present invention contemplates the use of detectable markers that are selectively expressed in a specific set or population of neurons. Thus, the marker can be expressed, for example, selectively in DA neurons and not in others.

In the case of *C. elegans*, as the organism is transparent, one may also be able to detect the colored products produced by such marker genes directly by the human eye. One major class of detectable marker genes that may be used to visualize a live *C. elegans* worm in its intact form comprise the fluorescent proteins such as the green fluorescent proteins (GFP). GFP is a naturally fluorescent protein which can be used to mark the cells in which a promoter is active. It has the benefit that the animals can be observed live.

The GFP proteins, originally isolated from the jellyfish *Aequorea victoria* retain their fluorescent properties when expressed in heterologous cells thereby provides a powerful tool as fluorescent recombinant probes to monitor cellular events or functions (Chalfie et al. 1994; Prasher 1995; WO 95/07463). Chalfie et al., in U.S. Pat. No. 6,146,826, (incorporated herein by reference), also describes the expression of GFP in *C. elegans* touch receptor neurons under the control of a promoter for the mec-7 gene which encodes a β-tubulin.

Several spectral and mutational variants of GFP proteins have since been isolated, for example, the naturally occurring blue-fluorescent variant of GFP (Heim et al. 1994; U.S. Pat. No. 6,172,188, both incorporated herein by reference), the yellow-fluorescent protein variant of GFP (Miller et al., 1999), and more recently the red fluorescent protein isolated from the coral *Discosoma* (Fradkov et al., 2000; Miller et al., 1999), which allows the use of fluorescent probes having different excitation and emission spectra permitting the simultaneous monitoring of more than one process. GFP proteins provide non-invasive assays which allow detection of cellular events in intact, living cells. The skilled artisan will recognize that the invention is not limited to the fluorescent proteins described and one may use any other spectral variant or derivative.

It is contemplated that one or more detectable markers may be used to monitor the viability of one or more neuronal populations simultaneously. For example, if the organism is subject to an free radical generator, or a environmental toxin, one can label DA neurons with one marker, the cholinergic neurons with another marker, the serotonergic neurons with yet another marker and study the effects of such a toxin on all the three neuronal populations simultaneously. In some embodiments, it is contemplated that the use of multiple markers may contribute to high-throughput screening.

Other detectable markers are also contemplated as useful. These include, β-galactosidase, enzymes such as such as urease, alkaline phosphatase, horseradish peroxidase, which can be detected either spectrophotometrically by the used of colorimetric indicator substrates that are typically employed with these detectable genes. These markers are somewhat limited in their use as they cannot be used to monitor live worms and worms must be killed and fixed to visualize detection.

In the case of β-galactosidase, lacZ is a stable enzyme, with negligible background activity in *C. elegans*. The chromogenic stain is stable, and the enzyme is still active after mild fixation. Generally, a lacZ with a nuclear localization signal, derived from SV40, is used so that the nuclei of cells expressing the construct can be identified.

It is also possible to attach antigenic polypeptides or short tags of amino acids to the native genes, and then detect expression patterns by using an antibody which is specific to the antigenic polypeptide or tag.

Detectable markers are generally known in the art and the skilled artisan will recognize that the invention is not limited to the examples described above.

C. Transporters and Neurotransmission

Chemical signaling by small molecule neurotransmitters, including glutamate, glycine, GABA, DA, NE, and 5HT, is terminated by transporter-mediated clearance (Rudnick and Clark, 1993). Pharmacologic or genetic disruption of transporter function elevates extracellular neurotransmitter levels, perturbs presynaptic transmitter homeostasis, and can trigger significant alterations in behavior (Giros et al., 1996; Pelham, 1997). The psychoactive agents cocaine and the amphetamines compete with substrates at amine (DA, NE, 5HT) transporters, with much of their addictive potential attributed to DAT blockade (Kuhar et al., 1991). In contrast, NE and 5HT transporter (NET and SERT, respectively) antagonists such as imipramine, desipramine, fluoxetine, and sertraline are important agents in the treatment of mood disorders, particularly depression (Barker and Blakely, 1995). The cloning of a rat GAT1 (Guastella et al., 1990) and a human NET (Pacholczyk et al., 1991) established the presence of a Na and Cl dependent transporter gene family whose members include transporters for most small neurotransmitters. The present inventors have previously cloned and characterized the C. elegans dopamine transporter gene, the T23G5.5 gene which encodes the CeDAT protein, and found that CeDAT is sensitive to antidepressants and cocaine (Jayanthi et al., 1998).

(i) Dopaminergic Transmission

Dopamine (DA), is a biogenic amine synthesized in the hypothalamus, in the arcuate nucleus, the caudate, and in other areas of the central and peripheral nervous system. Dopamine is also a precursor of other neurotransmitters, specifically, norepinephrine (NE) and epinephrine (E), in addition to being a neurotransmitter on its own. Dopamine and its agonists play important roles in cardiovascular, renal, hormonal, and central nervous system regulation through stimulation of alpha and beta adrenergic and dopaminergic receptors.

DA being a catechol and easily oxidized to a quinone, is often implicated as a generator of reactive oxygen species (ROS) like peroxide ($H_2O_2$), superoxide ($O^{2-}$) and hydroxyl radical $(OH)^-$ the latter being the most reactive and detrimental ROS. The dopamine transporter protein (DAT) is responsible for the uptake of excess dopamine that is released into the synaptic space back into neurons. Uptake of dopamine by DAT is important for regulating neuronal signaling as well as reducing the potential for DA being oxidized to form ROS.

(ii) Dopamine Transporter Protein (DAT)

DAT is a plasma membrane transport protein that controls extracellular DA concentrations, by recapture of DA that has been released during the process of neurotransmission, into nerve terminal. More recently, DAT has been recognized as a major target for various pharmacologically active drugs and environmental toxins (Miller, et al., 1999b).

DAT has been cloned and information regarding its structure and function are available (see review, by Chen, 2000, and the references cited therein). Chen (2000), describes that binding domains for dopamine and various blocking drugs including cocaine are likely formed by interactions with multiple amino acid residues, some of which are separate in the primary structure but lie close together in the still unknown tertiary structure. Other studies utilizing chimeric proteins and site-directed mutagenesis suggest the involvement of both overlapping and separate domains in the interaction with substrates and blockers. Recent findings using sulfhydryl reagents that selectively target cysteine residues support a role for conformational changes in the binding of DAT antagonists such as cocaine. The dopamine transporter can also operate in reverse, i.e., in an efflux mode, and recent mutagenesis experiments show different structural requirements for inward and outward transport.

DAT is also involved in various neurological and neuropsychiatric disorders ranging from Parkinson's disease to attention deficit disorder, schizophrenia, Tourette's syndrome, to drug abuse and addiction.

a. Sequence and Structure

DAT is a member of a large family of $Na^+/Cl^{2-}$ dependent transporters, which includes the norepinephrine (NE) transporter (NET) as well as transporters for serotonin, GABA, glycine, proline, creatine, betaine, taurine. Using sequences conserved between the GABA transporter and NET, DAT cDNAs have been cloned from rat, cow and human sources. DAT is a 619 (rat) or 620 (human) amino acid protein and the hydropathy and immunochemical data analysis indicate that DAT includes 12 transmembrane domains (TMDs), with both the amino- and carboxy-termini residing within the cytoplasm.

The generation of chimeric transporters produced by exchanging similar domains between the highly related DAT and NET transporters has provided clues as to the functional aspects of different DAT domains. It appears that residues within TMDs 1-3, or alternatively TMDs 9-12, greatly influence substrate affinities. TMDs 1-3 also influence affinity for certain DAT ligands such as GBR12395. TMDs 5-8 may also be critical in determining affinities for DAT and NET inhibitors such as cocaine and desipramine. The affinity of the DA neurotoxin MPP+ for the DAT is influenced by residues within TMDs 11-12.

b. DAT Gene Expression

The DAT gene is expressed largely in the CNS of mammals within a small subset of DA neurons and not in glia. As DAT expression is more restricted, than the expression of other genes such as the genes encoding DA biosynthetic enzymes such as, tyrosine hydroxylase (TH), aromatic amino acid decarboxylase, or the DA receptors, DAT provides an excellent marker for DA neurons and their projections.

In the rodent, DAT mRNA is found in great abundance within midbrain DA neurons of the substantia nigra, with somewhat lower expression in the ventral tegmental nuclei and adjacent nuclei. Within the hypothalamus, DAT is expressed within the A13 (zona incerta) and, to a lesser extent, the A14 (periventricular) and A12 (arcuate nucleus) cell groups, but not other TH-positive cell groups. Moderate DAT expression is also seen in the A16 cell group of the olfactory bulb. DAT mRNA is not found in regions devoid of DA cell bodies or within DA nerve terminals. In human brain, DAT mRNA exhibits the same general distribution as seen in rodents. Within human midbrain DA cells, the abundance of DAT mRNA is greatest within the ventral tier of the substantia nigra, followed by the dorsal tier and the ventral tegmental area, with the lowest levels of DAT mRNA seen within the retrorubral field.

The distribution of DAT immunoreactivity is largely consistent with other indices of DAT gene expression and the density of DA innervation. Thus, the striatum and nucleus accumbens are densely labeled, with labeling also apparent within the globus pallidus, cingulate cortex, olfactory tubercle and amygdala. DAT immunoreactivity is also seen in the perikarya, dendrites and axonal processes of midbrain DA neurons. Regional differences in somatodendritic DAT immunoreactivity covary with DAT mRNA levels and correlate with the susceptibility of subgroups of DA neurons to neurotoxins and idiopathic disease processes. DAT protein is localized primarily on extrasynaptic plasma membranes near aggregates of synaptic vesicles, consistent with DAT playing a key role in limiting the spatial domain of DA neurotransmission. Within the dendrites of midbrain DA cells, DAT is localized to plasma membranes and smooth endoplasmic reticulum, consistent with DAT-mediated dendritic DA release and/or DAT modulation of DA cell activity through its channel-like properties. Within perikarya, DAT is localized primarily to tubulovesicles, which may represent DA-containing membranes in transit.

c. DAT Gene Organization

The hDAT gene has been localized to chromosome 5p15.3 (35; 108), cloned and characterized. The gene spans 64 kb and is divided into 15 exons separated by 14 introns, with predicted intron-exon junctions. The hDAT coding region begins within exon 2 and extends partially into exon 15. A single transcriptional start site has been identified. There is no evidence for DAT RNA splice variants or the use of multiple polyadenylation sites. The overall exon-intron structure of the hDAT gene closely parallels that of the hNET (and to a lesser extent the serotonin and GABA transporter) gene. In general, each hDAT exon encodes a functional domain such as the N- or C-terminus or a putative TMD and adjacent hydrophilic loop. A number of Alu and other sequence repeats have been located within intronic portions of the gene. Of greater interest is a 40 bp variable tandem nucleotide repeat (VNTR) polymorphic sequence found in the 3' untranslated region just upstream of the polyadenylation site which may be associated with human diseases. A number of restriction fragment length polymorphisms have also been examined for such associations.

The 5' flanking sequences controlling transcription of the hDAT gene are interesting in that neither a canonical 'TATA' box nor a 'CAAT' box have been found, prompting the suggestion that the DAT is a TATA-less gene. The high local GC content and several putative SP1 sites might serve to direct DAT gene transcription. Other than the potential SP1 sites, a rather limited number of potential transcription factor response elements (such as, Egr-1, E-box, AP-2) may also comprise the proximal hDAT promoter, although individual elements have not been assessed functionally.

Recently, over 8 kb of hDAT 5' flanking sequence has been cloned (GenBank accession Number AF115382, incorporated herein by reference). Within this span of sequence, numerous potential regulatory sequences have been tentatively identified but, as with the core promoter, no genomic element that affords cell specific DA neuron expression has been identified. The development of midbrain DA cells is critically dependent on the expression of the nuclear receptor transcription factor nurr1, as proven by targeted disruption ("knockout") of the nurr1 gene. The nurr1 gene expression persists in rodent midbrain DA cells through adulthood, suggesting post-developmental functions as well. Interestingly, multiple nurr1 binding sites have been identified in 5'flanking sequences of the hDAT gene, and hDAT promoter constructs are activated by nurr1 co-transfection in vitro. Furthermore, the human homologue of nurr1 (NOT-1) is expressed at high levels in human midbrain DA neurons. Hypothalamic DA neurons express much lower levels of both nurr1 and DAT. Thus, it appears that the nuclear receptor nurr1/NOT-1 plays an important role in the maintenance, as well as development, of the strong DAergic phenotype seen in midbrain.

d. Psychostimulants and DAT Knockout Animals

DAT is a major target for psychostimulants such as cocaine, amphetamine and methamphetamine. The reinforcing properties of these drugs have been strongly correlated with their affinities for the DAT, in keeping with evidence implicating mesolimbic DA neurons in drug abuse. Cocaine and related drugs bind to the DAT and prevent DA transport. Amphetamines gain access to DA nerve terminals by both lipophilic diffusion across the plasma membrane and DAT-mediated transport, releasing DA from vesicular stores and evoking DAT-mediated DA release. In each instance, psychostimulants raise the extracellular concentrations of DA, likely augmenting DA neurotransmission over longer distances and/or durations, and causing behavioral activation.

Confirmation of these facts has been obtained by examination of DAT gene knockout animals. These mice exhibit significant locomotor hyperactivity in response to cocaine or amphetamine. In the absence of DAT, DA clearance time from the extracellular space is markedly prolonged (100-300 fold) and stimulants fail to further augment extracellular DA concentrations. It is interesting that this phenotype is accompanied by only 5 fold increases in extracellular DA, presumably due to profound (75-95%) decreases in the DA biosynthetic enzyme TH, DA levels, and DA release. Reduced expression of basal ganglia D1 and D2 DA receptors is also evident. In spite of low basal expression of DAT in the hypothalamus, the development of anterior pituitary hypoplasia and dwarfism in DAT knockouts suggests an unanticipated importance of the DAT in regulating pituitary function. The knockout mice are resistant to the DA neurotoxic effects of MPP+ and methamphetamine.

e. Potential Role of DAT in Human Disorders

DA neurotransmission has been implicated in various neuropsychiatric disorders, including Parkinson's disease, schizophrenia, Tourette's syndrome, attention-deficit disorder, and substance abuse. DAT is the primary DA-binding protein that functions to remove the neurotransmitter from the synaptic space. Given the nonredundancy of the gene, and its central role in controlling spatial and temporal aspects of DA neurotransmission, the DAT gene has received considerable attention as a candidate gene for DA-related neuropsychiatric disorders.

As mentioned above, characterization of the hDAT cDNA and gene has identified a VNTR. Although, the role of VNTRs in gene function remains obscure, recent evidence suggests that these repetitive elements could play a role in transcriptional and post-transcriptional gene expression. There are currently no data indicating that the VNTR in the DAT gene affects its expression. Nevertheless, the polymorphic VNTR serves as a highly informative marker for association and linkage analyses.

The DAT VNTR is 40 bp sequence that is present in the 3' nontranslated region of the DAT cDNA and is repeated 3-11 times. The most common allele contains 10 copies of the VNTR. In the US population, the frequency of the allele is 0.7 among Caucasians and Hispanics, and about 0.54 in African Americans. Among Asians, the frequency of the 10 copy allele is about 0.9, making the degree of heterozygosity in these populations quite low. The degree of ethnic heterogeneity in the DAT VNTR is an important consideration in interpreting disease association studies.

Perhaps the best evidence for involvement of the DAT with a disorder comes from work with attention-deficit hyperactivity disorder (ADHD). ADHD appears to be familial and heritable, and is perhaps the most common childhood-onset behavioral disorder. It is well recognized that ADHD patients benefit from treatment with certain psychostimulants, such as methylphenidate and amphetamine, which directly interact with the DAT. The evaluation of DAT as a candidate for susceptibility to ADHD using haplotype-based haplotype relative risk analysis. This study found a significant association of the 10 copy VNTR polymorphism with ADHD and undifferentiated ADHD. Similar results were independently obtained in an Irish population.

The DAT also has been proposed as a gene candidate for Parkinson's disease owing to the potential ability of DAT to transport neurotoxins into the DA neurons that are destroyed in the disease (Miller, 1999b).

DAT in Parkinson's Disease. PD is characterized by a substantial loss of midbrain DA neurons with a consequent loss of DA innervation to forebrain structures. The vulnerability of certain subgroups of DA neurons in PD and MPTP-induced parkinsonism correlates with higher basal levels of DAT gene expression. It is conceivable that avid transport of neurotoxins or even endogenous DA by the DAT may play a role in idiopathic PD.

Given the extent of DA cell loss, it is not surprising that significant decreases in DAT ligand binding sites are detected in PD striatum postmortem. DAT binding is reduced equivalently in progressive supranuclear palsy, a disease involving global degenerative changes throughout the basal ganglia and associated nuclei including the substantia nigra.

DAT in Alzheimer's Disease with Parkinsonism. Signs of clinical Parkinsonism occur in a sizable proportion (20-40%) of patients with Alzheimer's disease in the absence of classical neuropathology of PD. Alzheimer's subjects with parkinsonism exhibit a substantial loss of DAT in the caudate-putamen, albeit with a distribution which differs from the loss of DAT in idiopathic PD. There is also a significant decline in the number of DAT mRNA-positive DA cells in the midbrain, as well as lower DAT mRNA levels per cell. The profound loss of midbrain DA cells which occurs in PD, however, is not seen in parkinsonian Alzheimer's subjects, and TH expression is less impacted than the expression of DAT. DA-related gene expression, therefore, is impacted differently in Alzheimer's disease with parkinsonism than in idiopathic PD, although the underlying mechanisms are not understood. In nonparkinsonian Alzheimer's subjects, DAT and DA systems in general are minimally impacted.

DAT in Wilson's Disease. Wilson's disease is an autosomal recessive disorder involving mutations of the P-type copper ATPase ATP7B, resulting in excess copper deposition. Liver and brain are most affected. Varied neurological symptoms include parkinsonism, dystonia, and psychosis. Structural changes are seen in numerous brain regions including the striatum, where a loss of D2 receptors occurs. DAT ligand binding in vivo is decreased in Wilson's disease to the same extent as seen in PD, but without corresponding pathological changes in the substantia nigra. These preliminary data are somewhat reminiscent of the changes seen in Alzheimer's disease with parkinsonism and suggest a preferential loss of DA nerve terminals or a profound change in DAT biosynthesis, transport, or turnover.

DAT in Lesch-Nyhan Disease. This X-linked infantile onset disease, resulting from the loss of hypoxanthine-guanine phosphoribosyl transferase activity, leads to compulsive self-injurious behavior and movement disorders such as dystonia and choreoathetosis. Self-injurious behavior can be elicited in rodents by neonatal manipulations of DA function, and DA systems seem to be significantly impacted in Lesch-Nyhan. Striatal DAT density determined by PET imaging reported to be decreased 50-75% in a small group of Lesch-Nyhan subjects; other measures of DA function and total striatal volume are also significantly affected in this severe disorder.

DAT in Tourette's Syndrome. This disorder is characterized by symptoms including obsessions, compulsions, coprolalia and involuntary tics. Although the neuropathological mechanisms underlying Tourette's syndrome are unknown, the therapeutic benefit of decreasing DA neurotransmission is cited as evidence for the involvement of DA systems. A provocative study reported 37-50% increases in the density of DAT ligand binding in postmortem caudate-putamen from a small number of Tourette's syndrome subjects compared to controls. The concentrations of striatal DA and DA metabolites and DA receptor density were reportedly unchanged. More recently, a SPECT imaging study involving a small number of Tourette's subjects reported an equivalent (37%) increase in DAT density. It is speculated that an undetermined perturbation of DA systems in Tourette's syndrome may lead to a compensatory upregulation of striatal DAT.

DAT in Schizophrenia. The longstanding suspicion that DA systems are somehow involved in the etiology, symptomatology and/or treatment response of schizophrenia has led to investigations of DAT expression in this disorder. A functional study reported alterations in the Vmax and Km for DA uptake into cryopreserved nerve terminals from the striatum of schizophrenics relative to age- and sex-matched controls.

DAT in Chronic Stimulant Abusers. As discussed above, the DAT represents a major target protein for cocaine and amphetamine-like drugs. Chronic exposure to these drugs might therefore be expected to elicit compensatory changes in DAT expression. Thus, DAT is strongly implicated in drug addiction disorders.

(iii) CeDAT

Jayanthi et al. (1998) report the cloning and characterization of the *C. elegans* DAT (CeDAT). CeDAT is highly conserved with the mammalian catecholamine transporters with an amino acid identity of approximately 45%. The gene encodes a 615 amino-acid protein with 12 putative transmembrane domains. Mammalian cells expressing CeDAT exhibit saturable and high affinity $Na^+$- and $Cl^-$-dependent DA transport ($K_m$=1.2 µM) and are sensitive to the mammalian DAT antagonist GBR 12909 and cocaine, and to the substrate d-amphetamine at potencies comparable to their actions on human DAT in transfected cells (Jayanthi et al., 1998; Giros et al., 1992; Giros and Caron, 1993). CeDAT is also inhibited by the tricyclic antidepressant SERT antagonist imipramine and the NET-selective antagonist nisoxetine (Jayanthi et al., 1998). Mammalian DAT proteins are exclusively expressed in dopamine neurons.

Kyte-Doolittle hydrophilicity analysis suggested twelve hydrophobic stretches suitable for formation of TMDs that are well aligned with similar profiles of transporters in the gat1/net gene family. Two canonical sites for N-linked glycosylation are located in the large hydrophilic loop between TMDs 3 and 4, sites analogous to those known to be glycosylated in mammalian catecholamine transporters (Melikian et al., 1996). Additional N-glycosylation sites are present in the transporter's amino (N22) and carboxyl (N597) termini. The amino and carboxyl termini possess a number of Ser and Thr residues that may be targets for regulatory phosphorylation with two PKC sites (Ser45, Ser582) and one casein kinase II site (Thr580). A cAMP-dependent protein kinase site (Ser255) also lies in a putative intracellular loop between tmdsTMDs 4 and 5 within a span of residues (WKGXXTS-GKVVW (SEQ ID NO:3)) found in all catecholamine transporters. Similarly, a casein kinase II site between TMDs 6 and 7 lies in a highly conserved stretch of sequence (A(Y/F) SSYN(D/K)F (SEQ ID NO:4). Comparisons with other gat1/net family members demonstrates highest similarity of CeDAT to mammalian catecholamine transporters. CeDAT exhibits 47% amino acid identity with human, mouse, and bovine NETs, 43% identity with human, bovine, and rat DATs, 37% identity with human, rat and, mouse SERTs, and less than 35% identity with other gene family members. Sequence divergence suggests the carrier may have arisen from a common ancestral transporter before DATs, NETs, and ETS formed genetically distinct species. An Asp residue that is conserved in TMD1 of the DA, NE and 5HT transporters from fly to man (Kitayama et al., 1992; Barker and Blakely, 1995) but absent from GABA, glycine, taurine, proline, creatine and taurine transporters, is also present in an analogous position (D60) in CeDAT. Thus, there is sequence divergence and conservation that is evident comparing CeDAT with its most closely related mammalian homologs.

D. Expression Vectors

Within certain embodiments, expression vectors are employed to express a detectable marker, such as a GFP polypeptide, beta-galactosidase, or an antigenic polypeptide. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Throughout this application, the term "expression construct" is meant to include any type of genetic construct containing a nucleic acid coding for a gene product in which part or all of the nucleic acid encoding sequence is capable of being transcribed and translated into a polypeptide product. An "expression cassette" is defined as a nucleic acid encoding a gene product under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

By attaching a tissue-specific or cell-specific promoter region of a nucleic acid to a reporter or a detectable marker, one can obtain tissue-specific or cell-specific expression of the nucleic acid of interest. C. elegans promoter elements tend to be relatively short, often less than 1 kb. Both transcriptional and translational fusions can be made.

To derive neuronal expression of marker genes some promoters contemplated useful in context of the present invention include the dopamine transporter promoter, the tyrosine hydroxylase promoter (encoded by the cat-2 gene), the cha-1 promoter (expressed in cholinergic neurons), an acr-2 promoter (expressed in cholinergic motor neurons), an unc-30 promoter (expressed by GABA-ergic neurons), or an unc-4 promoter (expressed by A-class motomeurons).

In the case of the dopamine transporter promoter the present inventors have shown that a ~700 bp region of the CeDAT promoter region is responsible for DA neuron specific reporter expression. The CeDAT promoter regions are also described in SEQ ID. NO. 1.

The use of other C. elegans promoters which are well-known in the art to achieve expression of a coding sequence of interest are contemplated as well, provided that the levels of expression are sufficient for a given purpose.

In addition, the use of other viral or mammalian cellular or bacterial phage promoters which are well-known in the art to achieve expression of a coding sequence of interest are contemplated as well.

By employing a promoter with well-known properties, the level and pattern of expression of the protein of interest following transfection or transformation can be optimized. Further, selection of a promoter that is regulated in response to specific physiologic signals can permit inducible expression of the gene product.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

E. Screening for Modulators of Neuronal Viability and/or Signaling

The present invention comprises methods for screening for a variety of substances, including substances that affect neuronal viability; substances that inhibit neuronal cell death; substances that prevent neuronal degeneration; substances that cause neuronal degeneration, and/or substances that modulate neuronal signaling and function. The present invention further comprises genetic methods for identifying modulators of neuronal signaling such as modulators of DAT, modulators of dopamine signaling and/or other elements that modulate presynaptic signaling.

These assays may comprise random screening of large libraries of candidate substances; alternatively, the assays may be used to focus on particular classes of compounds selected with an eye towards structural attributes that are believed to make them more likely to modulate the function of neuronal cells, such as known neurotoxins, neurotransmitter transporter agonists and antagonists, addictive substances, pesticides, therapeutic substances, monoamine oxidase inhibitors, and antioxidants.

By function, it is meant that one may assay for the expression of a detectable marker expressed selectively in some neuronal populations. A decrease or loss in the expression of the marker indicates neuronal cell death, apoptosis, degeneration, and/or decrease in neuronal viability. On the other hand, no difference in the expression of the marker indicates that the cells were either protected from degeneration (if a second substance is used) or were not affected by the substance. The preferred detectable marker is a fluorescent protein as it allows for longitudinal studies on live animals, although other markers such as beta-galactosidase, enzymes that react to produce colored reaction products, may also be used.

To screening for substances that, affect neuronal viability; and/or ability to prevent neuronal degeneration; and/or cause neuronal degeneration; and/or inhibit neuronal cell-death, a method will generally comprise: (a) providing a *C. elegans* that expresses a detectable marker in a neuronal cell; (b) exposing the *C. elegans* to a candidate substance; and (c) detecting a change in the expression of the marker relative to the expression of the marker before said exposing; wherein a change in the expression of the marker corresponds to a change in the viability; and/or ability to prevent neuronal degeneration; and/or ability to cause neuronal degeneration; and/or ability to inhibit neuronal cell-death, of the neuron.

To identify a modulator of dopamine transporter protein (DAT), one generally will determine the function of DAT in the presence and absence of the candidate substance. A modulator is defined as any substance that alters function. For example, a method generally comprises: (a) obtaining a recombinant *C. elegans* that expresses a detectable marker in a dopaminergic neuronal cell; (b) exposing said *C. elegans* to a candidate substance; (c) exposing said *C. elegans* to a neurotoxin that requires a dopamine transporter for intracellular access; and (d) detecting any change in the expression of the GFP after step (c), wherein a difference between the measured characteristics, i.e., expression of marker, indicates that said candidate modulator substance is, indeed, a modulator of the DAT.

The invention also describes genetic screening that is aimed at identifying the genetic component of the modulators of neuronal signaling. Such a method of screening for molecules that modulate neuronal signaling comprises: (a) obtaining a recombinant *C. elegans* that expresses a detectable protein in a neuronal cell which is a knockout and/or a mutant for a component of neuronal signaling; (b) obtaining a second recombinant *C. elegans* that expresses a detectable protein in a neuronal cell which is a (or another) mutant for a component of neuronal signaling; (c) comparing the differences in neuronal viability when exposed to a neurotoxic substance in the *C. elegans* of step (a) with the *C. elegans* of step (b); and (d) identifying the genetic component of the mutation.

Assays may be conducted in cell free systems, in isolated cells, or in organisms including transgenic animals, recombinant animals, mutated animals. A preferred embodiment uses live animals as this represents the most intact physiology and permits high-throughput screening.

It will, of course, be understood that all the screening methods of the present invention are useful in themselves notwithstanding the fact that effective candidates may not be found. The invention provides methods for screening for such candidates, not solely methods of finding them.

(i) Modulators

As used herein the term "candidate substance" refers to any molecule that may potentially inhibit or enhance DAT activity. The candidate substance may be a protein or fragment thereof, a small molecule, or even a nucleic acid molecule. It may prove to be the case that the most useful pharmacological compounds will be compounds that are structurally related to cocaine, methylphenidate, etc. Using lead compounds to help develop improved compounds is know as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

An inhibitor according to the present invention may be one which exerts its inhibitory or activating effect upstream, downstream or directly on neuronal viability and neuronal signaling. Regardless of the type of inhibitor or activator identified by the present screening methods, the effect of the inhibition or activation by such a compound results in differences in neuronal viability or neuronal signaling as compared to that observed in the absence of the added candidate substance.

(ii) In Vivo Assays

In vivo assays involve the use of various animal models, including transgenic animals that have been engineered to have specific defects, or carry markers that can be used to measure the ability of a candidate substance to reach and effect different cells within the organism. Due to their size, transparency, ease of handling, and information on their physiology and genetic make-up, *C. elegans* are a preferred embodiment.

In such assays, one or more candidate substances are administered to an animal, and the ability of the candidate substance(s) to alter one or more characteristics, as compared to a similar animal not treated with the candidate substance(s), identifies a modulator. The characteristics may be any of those discussed above with regard to the neuronal viability, inhibition of neuronal degeneration/cell death, or neuronal signaling.

Treatment of these animals with test compounds will involve the administration/exposing of the compound, in an appropriate form, to the animal. Administration or exposing of the compound to a worm is by adding the compound to a liquid suspension and transferring the worms to this suspension prior to replating the worms on solid media. More details are described in the section entitled as 'Examples'.

Determining the effectiveness of a compound in vivo may involve a variety of different criteria. Also, measuring toxicity and dose response can be performed in animals in a more meaningful fashion than in in vitro or in cyto assays.

(iii) Genetic Assays

Other genetic assays that comprising crossing a *C. elegans* that bears a mutation in a neuronal signaling component with a *C. elegans* that is a knockout for a neuronal signaling component may be performed. In such an assay, if the progeny of the cross demonstrates a rescue of the phenotype, this indicates that the mutation in the mutant strain is in a gene other than the gene of the knockout. One can then identify the mutation and isolate and identify the gene corresponding to the mutation using the powerful genetics of *C. elegans*.

a. Setting Up Crosses

Although *C. elegans* is a self-fertilizing hermaphrodite it is possible to set up genetic crosses as functional males are found (albeit rarely) and male sperm outcompetes hermaphrodite sperm. Wild type *C. elegans* males are found at about 0.05% of the population. They develop after accidental non-disjunction of the X chromosomes in gametogenesis (males are XO). The rate of non-disjunction can be increased by exposing a population of hermaphrodites to heat shock (30° C. for >6 hrs), and "male lines" can be propagated indefinitely by picking individual males and hermaphrodites. In addition, several loci have been described which when mutated result in high levels of males in a population. These Him strains, such as those carrying the him-8 mutation, can be used to generate males carrying desired mutations for crossing by mating with mutant hermaphrodites. When a hermaphrodite is mated, the male sperm outcompetes her own supply, and the progeny are thus almost entirely cross-fertilized.

F. Transgenic, Knockout and Mutant *C elegans*

In an exemplary embodiment, the "transgenic animals" of the invention are produced by introducing transgenes into the germline of the of the animal. Different methods can be used for the introduction of transgenes. The specific line(s) of any animal used to practice this invention are selected for general good health, good embryo yields, and good reproductive fitness.

The early germline of *C. elegans*, which are hermaphrodites, is syncytial, i.e., individual nuclei reside in pockets of cytoplasm but are connected to a central rachis. This facilitates uptake of any nucleic acid injected into the syncytial gonad by multiple nuclei. However, the germline nuclei that take up the nucleic acid, such as a DNA vector bearing the nucleic acid encoding a polypeptide of interest, have a repair machinery that catenates the nucleic acid into long extrachromosomal arrays (>100 kb) which are maintained in the resultant offspring with relatively stability. The transgenic nematodes are selected by co-injecting a visible marker gene, usually a dominant mutation in the cuticular collagen gene rol-6(su1006). This gene causes the nematodes to develop a helically twisted cuticle and to roll longitudinally when they move forward.

Transgenesis can be used for several sorts of analysis including as a proof that a DNA fragment contains the wild-type copy of a mutated gene, by rescuing the mutant with the transgene. Transgenic animals maybe used to generate "antisense knockout" strains. In such embodiments, if the open reading frame of the nucleic acid is attached "backwards" to its own promoter, antisense RNA will be made, which suppress translation of the wild type mRNA. In other embodiments, analysis of promoter elements can be performed by ligating the 5' region of a nucleic acid to detectable marker genes, for example to the enymatic markers such as lacZ or beta-galactosidase, or to fluorescent reporters/markers, such as the green fluorescent proteins. Transgenic *C. elegans* may also be used to drive the overexpression of a nucleic acid to look at gain-of-function mutations in the gene encoded by the nucleic acid. One may also introduce in vitro mutagenized or foreign genes to examine structure-function relationships and to constructing complexly mutated strains.

Transgenic extrachromosomal arrays can be stably integrated into the chromosomes by UV irradiation of transgenic lines, or by coinjection of single stranded DNA. Homologous recombination is very rare in *C. elegans*.

The progeny of the transgenically manipulated worms can be tested for the presence of the construct by any of the following: 1) by observation of altered behavior due to the transgene; 2) by Southern blot analysis of a segment of tissue; 3) by PCR amplification of genomic DNA; and/or by co-injecting a fluorescent marker with the transgene and observing the retention of fluorescence of the transgenic marker in the DNA. If one or more copies of the exogenous cloned construct remains stably integrated into the genome of such transgenic *C. elegans*, it is possible to establish permanent transgenic lines carrying the transgenically added construct.

The litters of transgenically altered worms can be assayed after birth for the incorporation of the construct into the genome of the offspring. Preferably, this assay is accomplished by hybridizing a probe corresponding to the DNA sequence coding for the desired recombinant protein product or a segment thereof onto chromosomal material from the progeny. Those progeny found to contain at least one copy of the construct in their genome are grown to maturity.

The "knockout animals" of the invention can be produced either by generating transgenic animals as described above or by mutagenesis of the animal. Different mutagenesis methods can be used. The specific line(s) of any animal used to practice this invention are selected for general good health, good embryo yields, and good reproductive fitness. In addition, the haplotype is a significant factor.

The gene knockout strategy for generating knockout *C. Elegans* involves using a random mutagen, such as trimethylpsoralen, or EMS, to mutagenize a very large number of worms (see http://info.med.yale.edu/mbb/koelle/protocols/protocol_Gene_knockouts.html, *C. elegans* Gene Knockout Protocols, by Michael Koelle, Heather Hess, David Shechner). Briefly, the worms are divided into many small subcultures and allowed to have progeny. A portion of each subculture is stored alive in the freezer, and genomic DNA is made from the rest of the culture. Therefore, the DNA made from the siblings of the frozen worms and carries the same mutations as the frozen worms do.

At a very low frequency (~1/400,000 mutagenized genomes) the mutagenesis produces a small deletion (~200-4,000 bp) in any gene of interest to generate knockouts. At a high frequency the mutagenesis produces point mutants. For the knockouts, PCR primers flanking the gene of interest are used to amplify from the genomic DNA samples, deletions can be detected because primer sites flanking such a deletion will be brought closer together and will generate a PCR amplicon smaller in size than that amplified from wild-type genomic DNA. When the PCR reaction is carried out under appropriate conditions small deletion amplicons are amplified much more efficiently than the larger wild-type amplicon. Thus DNA representing several thousand mutagenized genomes can be amplified in a single reaction and a deletion amplicon generated from just one of those genomes will still be detected on an ethidium bromide stained agarose gel. Once a DNA pool containing a deletion is thus identified, one can work back to identify the subculture of worms in which the deletion occurred, the frozen worms from that subculture can be thawed, and live animals carrying the deletion mutation can be identified.

G. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Construction of Recombinant *C. elegans* Expressing Detectable Markers Methods

Strains and Maintenance

*C. elegans* strains were cultured on either OP-50 or NA-22 at 22.5° C. according to standard methods (Brenner, 1994). The N2 Bristol strain is the wild-type strain and can be obtained from the *Caenorhabditis* Genetics Center (University of Minnesota, Minneapolis, Minn.).

Plasmid Construction

The DAT-1 transcriptional GFP fusion (Pdat-1::GFP) was created by PCR amplification of the DAT-1 regulatory region in cosmid T23G5.5. The amplified product immediately upstream of the initiating codon ATG was digested with HindIII and BamHI, and the resultant 0.7 kb fragment was cloned into the HindIII and BamHI sites of the GFP reporter vector pPD95.73 (gift from Andy Fire), to create the construct called pRN200.

Germline Transformation

Transgenic animals were generated as previously described (Mello et al., 1991; Mello and Fire, 1995). Transgenic animals containing the transcriptional fusion (pRN200) were obtained after co-injection of 20 ng/μl of pRN200, 30 ng/μl of plasmid carrier DNA (pBluescript), and 50 ng/μl of pRF4 (rol-6(su1006)) (Kramer et al., 1990) into the gonads of the N2 strain. Animals were cultured at 24.5° C., and F1 and F2 transgenic animals were selected by their roller phenotype. The transgenic array containing the dat-1 transcriptional fusion was then integrated into the genome using irradiation-based recombination. Two independent integrants were isolated and both display similar GFP expression patterns; one integrant, RN200, was outcrossed four times and used for subsequent analysis (now called RN200×4). RN200×4 was mapped to within 2.4 MU from dpy-11 on chromosome V.

6-OHDA Assays

Synchronized cultures of nematodes were prepared by collecting gravid worms from one or two 100 mm 8P/NA22 plates, washing them 2 times in approximately 10 mls dH2O (2,000 rpm for 2 min), and incubating them in alkaline hypochlorite for 7-10 min. essentially as described (Emmons et al., 1979; Epstein and Shakes, 1995). Following the 17-24 hour incubation in M9 to obtain the synchronized L1's, the worms were washed once in 10 mls dH2O, spread on 8P/NA22 plates and incubated at 24° C. for 25-29 hours. The L3 larvae were collected, washed once or twice in dH2O, and added to the assay mix (to a final OD600 worms of 0.1-0.2) containing 10 mM ascorbic acid containing 10 or 50 mM 6-hydroxydopamine +/−10 mM d-amphetamine or 1 mM imipramine. The assay mix (1-2 mls) was incubated for 1 hour at 24° C., and mixed gently every 15 min. The worms were then washed in 0.5-1 ml dH2O as above and spread on NGM/OP50 plates. The worms were examined and scored 40-80 hours post-6-OHDA exposure on 2% agarose pads, using 2% NaN3 to immobilize them. For electron microscopy, the worms are fixed approximately 60 hours following exposure to 6-OHDA.

Scoring of the CEPs were performed by applying approximately 50-60 worms on the agar pad, and examined under a Zeiss M2 fluorescent dissecting scope. All 4 CEP dendrites were examined in each worm and the GFP fluorescence within the dendrites followed from the nerve ring to the tip of the nose. If any part of the dendrite was absent, the worm was considered to have altered CEPs. The DA neurons were examined in living animals using a Zeiss Axioskop with a planApo 40 and 63× objective and a Zeiss LSM410 confocal laser-scanning microscope.

Scoring of the CEPs were performed on a Zeiss M2 fluorescent dissecting scope using a 2× and 10× objective. For electron microscopy, worms were fixed in buffered (100 mM Hepes, pH 7.5) 3% glutaraldehyde, followed by postfixation in buffered 1% OsO4 (Hall, 1995; Sulston and Hodgkin, 1988). After encasement in 1% agar, samples were dehydrated and embedded in Polybed 812 resin (Polysciences). Serial sections were poststained in uranyl acetate followed by lead citrate.

Example 2

Screening for Modulators of DAT

For the genetic and pharmacological evaluation of DAT and genes involved in altered DA neurotransmission, the *C. elegans* dopamine transporter (CeDAT) was cloned as described in Jayanthi et al., 1998, incorporated herein by reference.

Figure 1B:
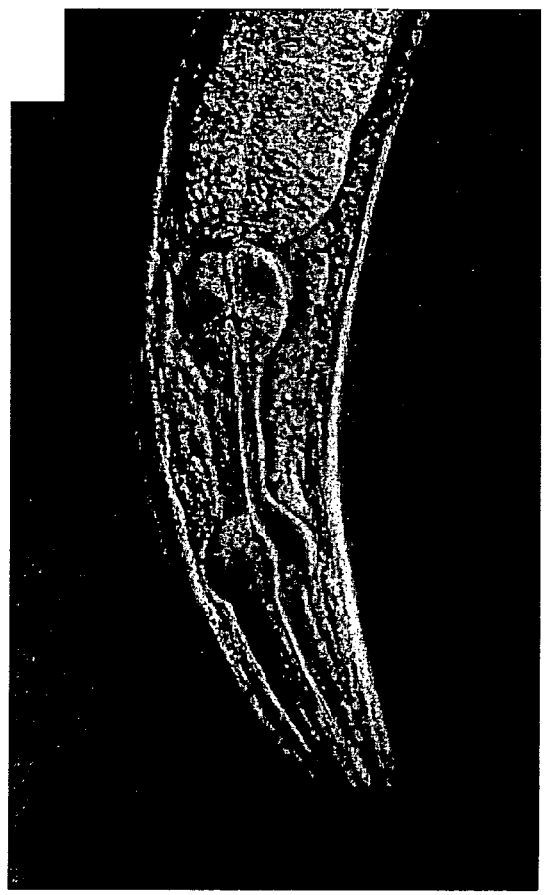

Following the initial observation that a genomic fragment comprising the CeDAT gene (2.1 kilobase pair fragment upstream of the start ATG to 0.7 kb downstream of the ATG) was sufficient to drive reporter expression in DA cell bodies (T. Ishihara, personal communication; See 1. Hope, worn expression pattern for gene T23G5.5 (http://bgypc086.leeds.ac.uk), an integrated transgenic line expressing a CeDAT promotor-GFP fusion ($P_{CeDAT}$::GFP) containing 717 bp immediately upstream of the start ATG was created. This line displays intense GFP expression in all eight DA neurons within the hermaphrodite, but is not evident in other cells (FIG. 1). The axons and dendrites in these transgenic animals are clearly visible and can be easily observed as the animal moves under a fluorescent dissecting scope.

Screening. In order to set up a screen for molecules involved in DA neurodegeneration in *C. elegans*, a well-defined behavior dependent on the normal DAergic function is required. Alternatively, visualization of changes in morphology of the DA neurons can be used as a screening tool. As DA mediated behaviors are relatively subtle in *C. elegans* screening a large number of worms based on the modification of these behaviors could be tedious, a more efficient and robust screening method is to select for mutants within the transgenic lines expressing GFP that have altered DA neuronal morphology. Thus, GFP expressing *C. elegans* that are mutant in DA neuronal morphology were used.

Toxin Lesioning. The neurotoxins 6-OHDA and MPP$^+$ provide cell-specific lesions reminiscent of the selective pathology of PD and are used as tools to probe the mechanism of environmentally triggered DAergic neural degeneration in animal models of PD (Yahr and Bergmann, 1986, Lotharius et al., 1999; Miller et al., 1999).

*C. elegans* DA neurons were also selectively degraded by 6-OHDA which enters the cells via CeDAT. Briefly, the worms are exposed to the neurotoxin (or any other candidate substance) dissolved in a liquid suspension prior to being replated on a solid plate.

Exposure to toxins is carried out by transferring the worms to a solution of water containing 10 mM Ascorbic Acid and 10-50 mM 6OHDA in a final volume of 600 µl. The worms are incubated for 1 hour at 22-24° C. with mixing in silica coated tubes. The exposing is stopped by dilution with 1 ml of water. The tube is then pulsed at 2000 rpm for 2 minutes, resuspended in water and the worms are spread on N6M plates (100 mM plates) coated with OP50 *E. coli*, which the worms feed on.

Accordingly, a specific loss of the GFP expression in those neurons that expressed CeDAT was observed in the transgenic lines following exposure to the toxins. Based on this, a genetic screen for the retention of GFP in DA neurons following toxin exposure is contemplated.

Genetic Screening. The present inventors contemplate performing genetic screens based on the strategy described below. To establish the screen, the integrated transgenic line carrying the transcriptional reporter $P_{CeDAT}$::GFP will be used. Following mutagenesis of the last larval stage of the worm (i.e., the L4 stage, where the maximum number of gametes are present in the hermaphrodite), the F2 generation (second generation of the mutagenized worm) will be subject to 6-OHDA or MPP$^+$ and tested for loss of toxin sensitivity. As most mutations are recessive, screening in the F2 generation allows the mutations to become homozygous and therefore increases the likelihood of a modified phenotype. All mutants recovered will then be physically mapped using a two-factor linkage analysis, and the genetic map interval defined by three-factor crosses (Sulston and Hodgkin, 1988). Once the area of the mutated allele has been identified, candidate genes can be tested through microinjection of cosmid spanning the gene. The inventors further contemplate assaying whether DA neuron-specific expression of the wild-type gene rescues sensitivity to 6-OHDA. Finally, the impact of coexpression of CeDAT or mammalian DAT with the identified protein or its mammalian homolog (if one has been identified) following toxin exposure in mammalian cells will be performed.

Figure 2:
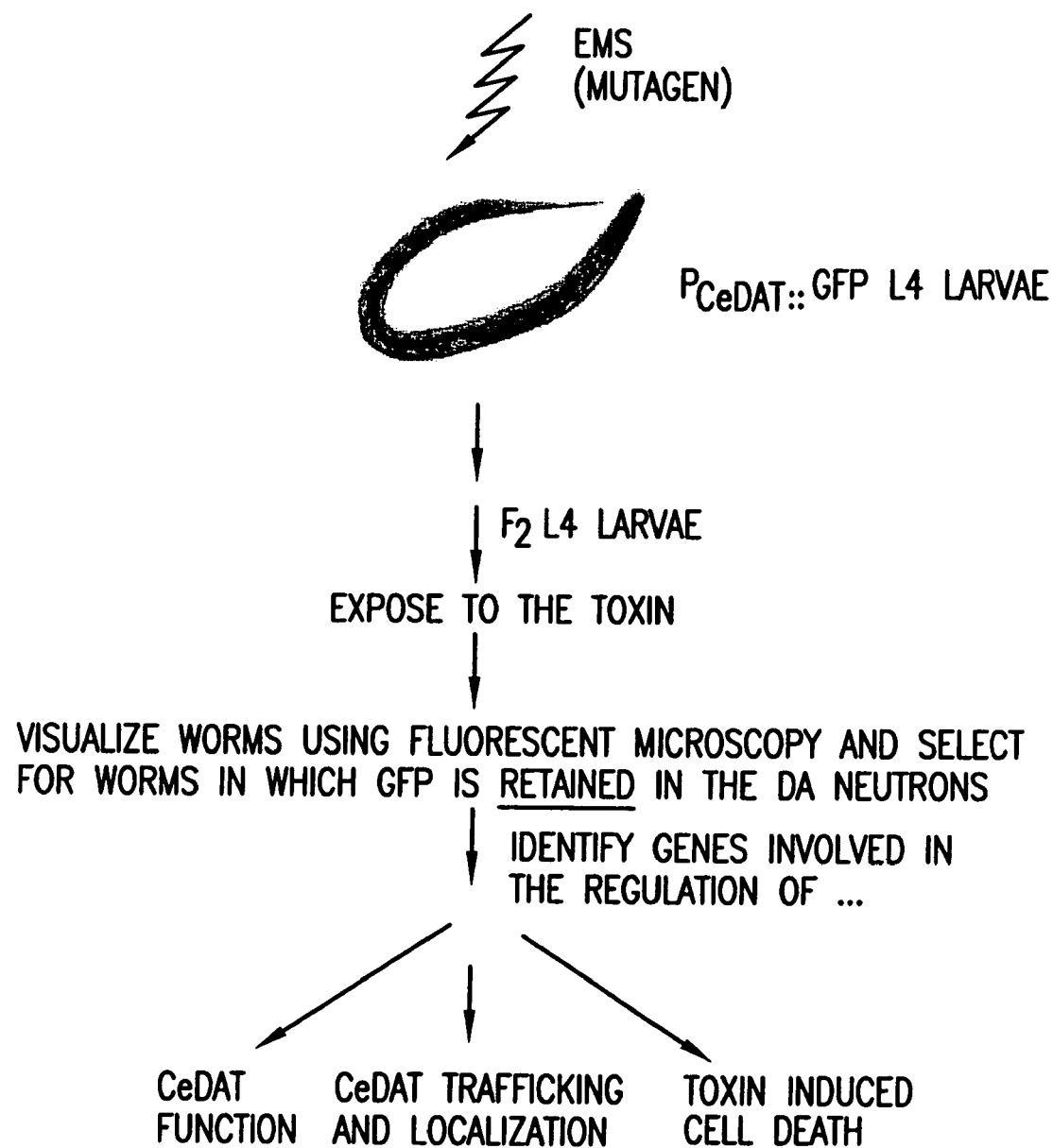
FIG. 2. Genetic screens to identify CeDAT mutants, CeDAT regulators, and determinants of toxin sensitivity using ethylmethanesulfonate (EMS).
Figure 3A:
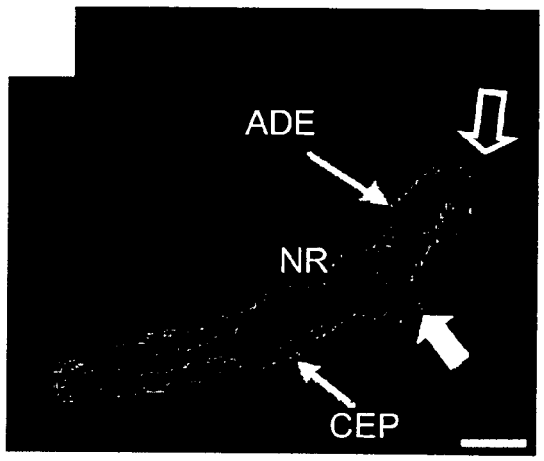
FIGS. 3A, 3B, 3C & 3D. Direct visualization of DA neurons in living *C. elegans*.
Figure 3B:
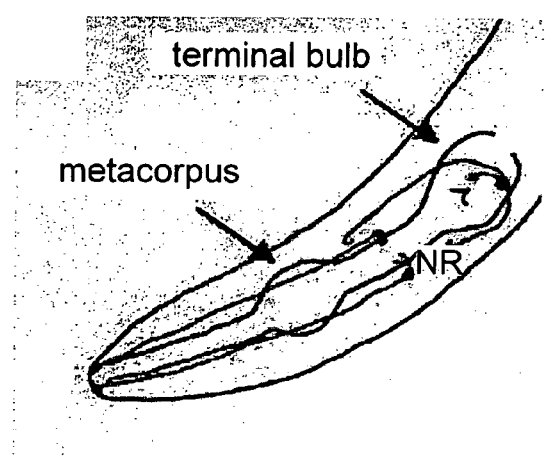
Figure 3C:
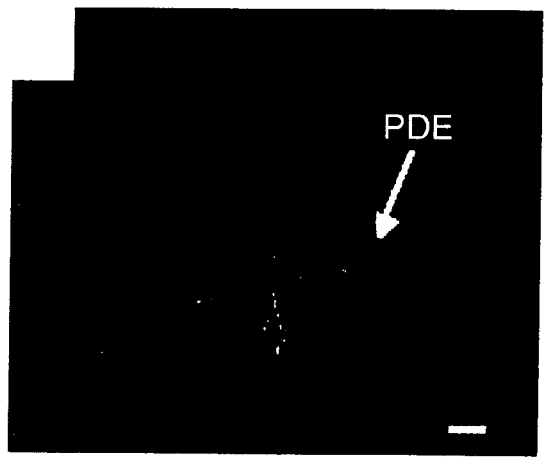
Figure 3D:
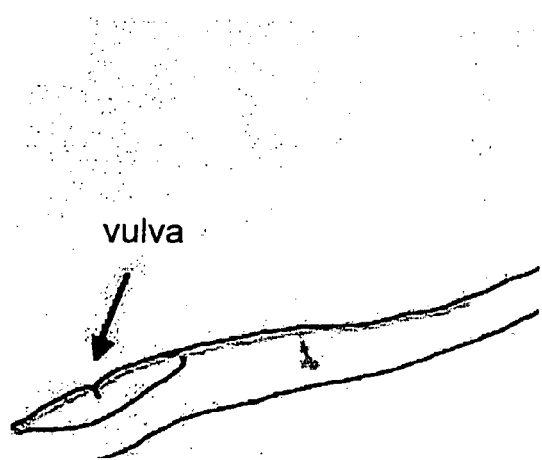
Figure 4B:
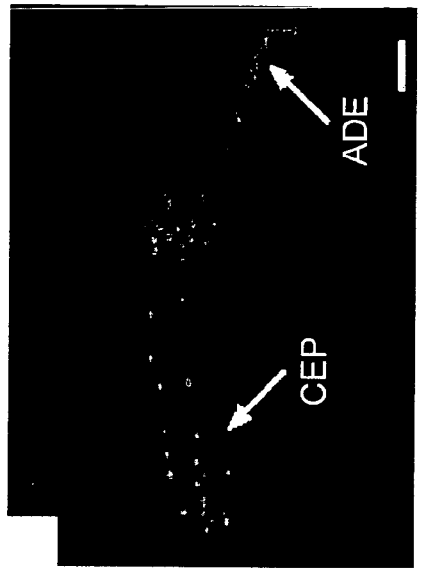
FIGS. 4A, 4B, 4C, 4D, 4E & 4F. Effect of 6-OHDA on GFP signal in DA Neurons.
Figure 4D:
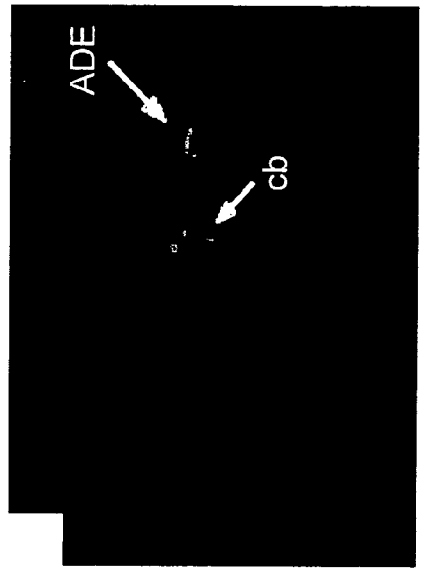
Figure 4A:
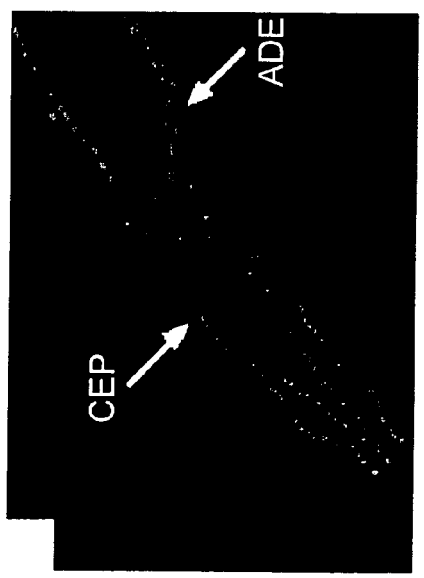
Figure 4C:
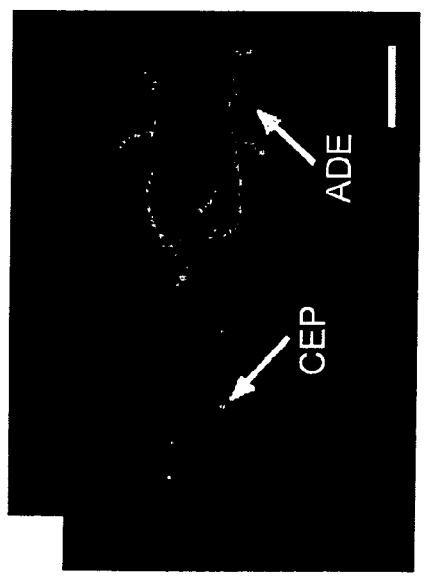
Figure 4F:
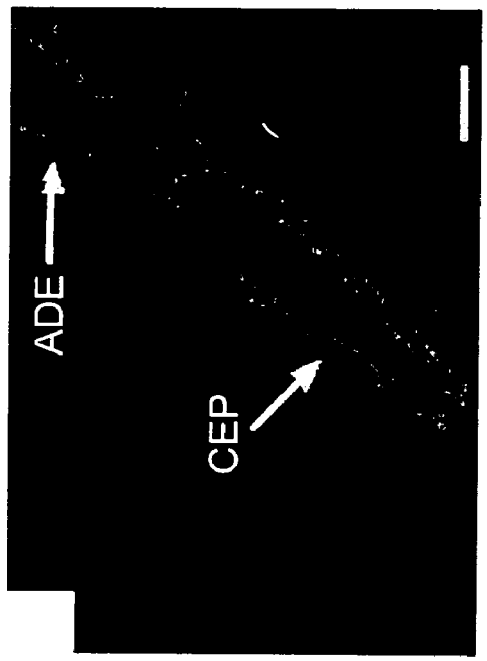
Figure 4E:
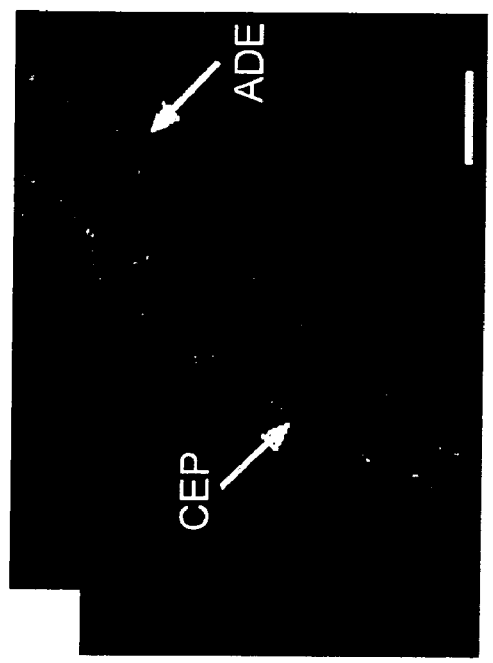
Figure 5A:
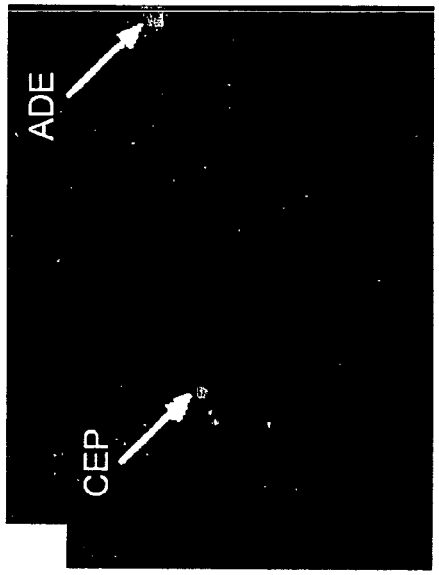
FIGS. 5A, 5B, 5C, 5D, & 5E. Dependence of apparent 6-OHDA toxicity on DAT-1.
Figure 5B:
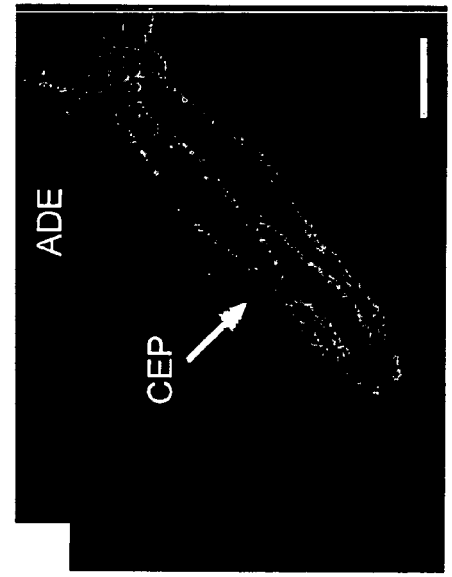
Figure 5C:
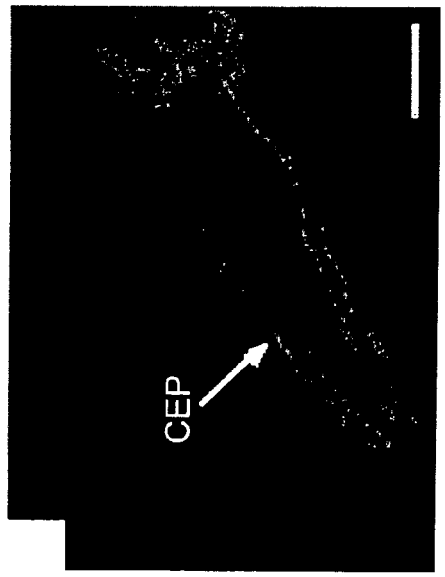
Figure 5D:
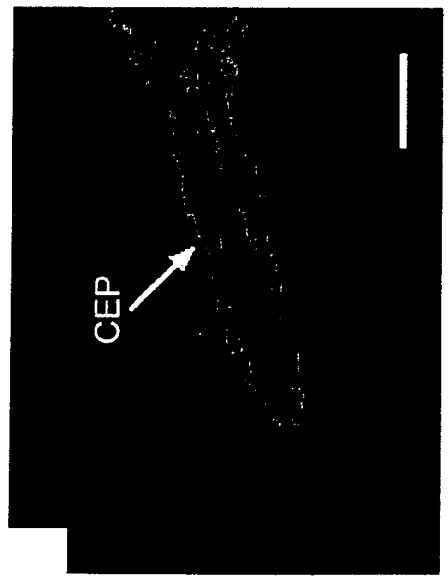
Figure 5E:
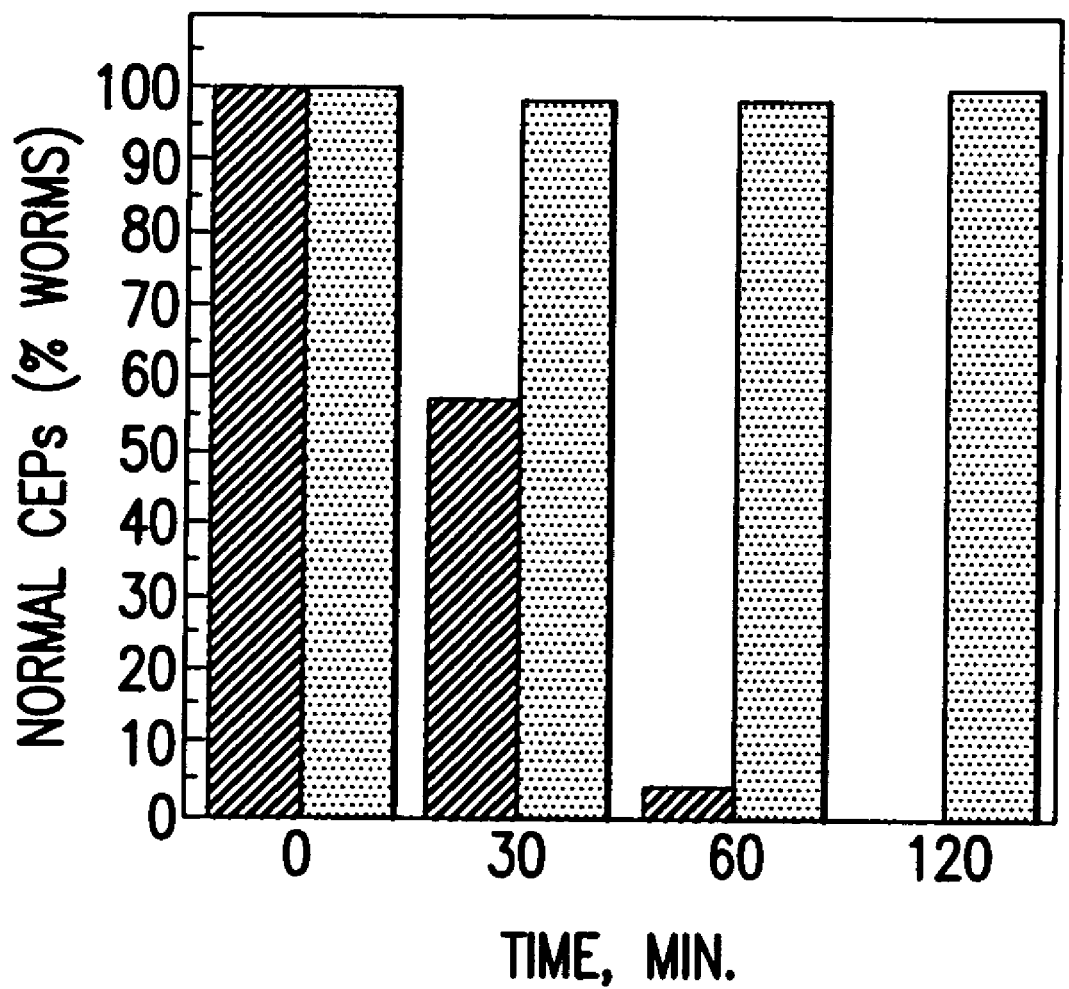
Figure 6B:
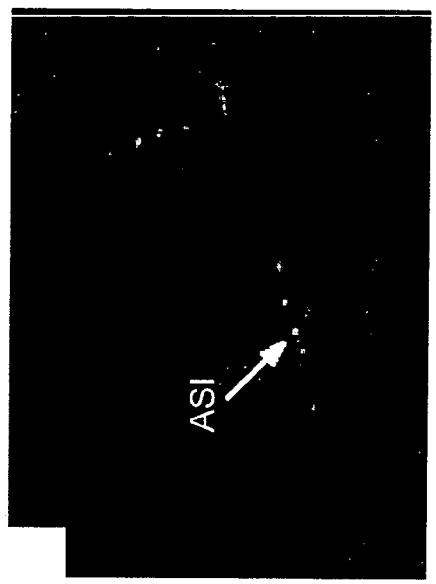
FIGS. 6A, 6B, 6C & 6D. Transfer of the DAT gene product sensitizes non-DA neurons to 6-OHDA.
Figure 6A:
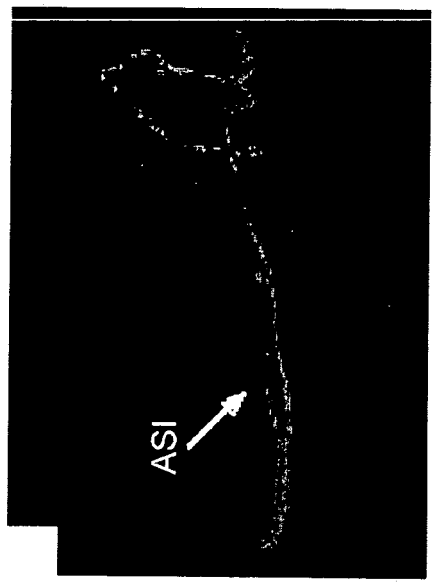
Figure 6D:
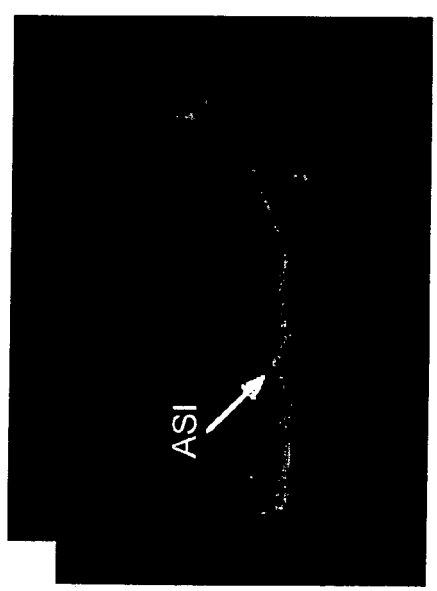
Figure 6C:
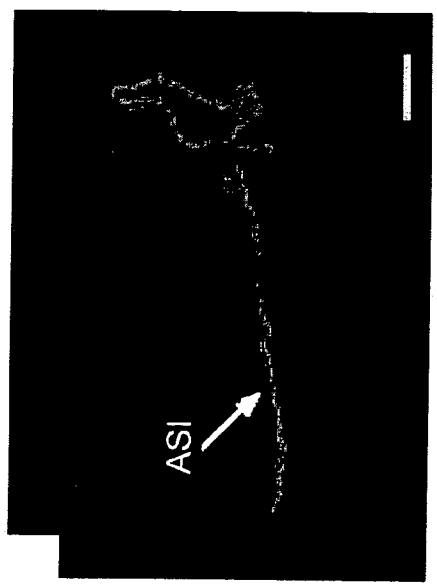

The genetic screen is also described in FIG. 2. Following mutagenesis and toxin exposure, any retention of GFP within a DA neuron is due to either the inability of the toxin to enter the cell (for example via CeDAT), suppression of some mediator of toxin sensitivity, or inhibition of neuronal degradative pathway(s).

Analysis of Mutants. The inventors contemplate that the methods described will identify CeDAT mutants that are regulators and modulators of CeDAT. Since DATs are required for toxin accumulation in mammalian DA neurons, the inventors expect to recover an allelic series of mutations in CeDAT which would modify its activity, as well as regulators and modulators of CeDAT. A variety of CeDAT mutants that limit the toxin's ability to enter the cell (and hence alter GFP expression), including those affecting transporter activity, stability, and localization, are also expected to be identified in the screen. These mutants would be especially valuable because the structural basis for DA transport and DAT regulation are poorly defined. Furthermore, the availability of DATs at the nerve terminals has been proposed to play a role in the vulnerability of DAergic neurons to PD, and this screen should assist in delineating its role in the neurodegeneration (Miller et al., 1999).

The inventors also contemplate experiments where high-affinity antibodies raised against CeDAT should be able to partition these mutants into their proper complementation groups. Finally, since DAT plays a principle role in DA homeostasis and abnormal DA neurotransmission and has been indicated in a variety of other neuropsychiatric disorders including schizophrenia, drug addiction, Tourette's Syndrome, and Attention Deficit Hyperactivity Disorder, novel regulators identified from this screen could aid in understanding pathophysiology of these diseases (Gainetdinov et al., 1998; Miller et al., 1999).

Toxin Sensitivity. The inventors have shown that *C. elegans* DA neurons are vulnerable to mammalian DA neuronal toxins (Nass et al., 2000). A loss of reporter expression in DA neurons was seen following 6-OHDA treatment using the GFP constructs described above. A CeDAT deficient line has been established ((Nass et al., 2000; J. Duerr and J. Rand, personal communication). Using this line the inventors contemplate that CeDAT antagonist will reduce or eliminate toxin sensitivity. If the 6-OHDA action truly reflects DA neuron toxicity, one may also expect to see behavioral deficits like those seen after laser and genetic ablations of DA neurons (Lints and Emmons, 1999; Duerr et al., 1999; Sawin et al., 2000).

The inventors also contemplate identifying molecular determinates of toxin sensitivity of DAT. For example, 6-OHDA and $MPP^+$ appear to confer DA neuronal death via impairing cellular ROS homeostasis, although their mechanism of action in vivo remains unclear (Yahr and Bergmann, 1986; Lotharius et al., 1999). Both toxins inhibit complexes in the mitochondrial transport chain (6-OHDA, complex I and IV, $MPP^+$, complex I) (Glinka et al., 1997; Kopin, 1992). 6-OHDA is also easily oxidized to generate hydroxyl radicals and the superoxide ion and can covalently interact with cysteinyl groups to inhibit protein function (Cohen and Heikkila, 1974; Graham et al., 1978). It is debatable whether $MPP^+$ confers toxicity via inhibition of mitochondrial function since a cell which does not have mitochondria is also sensitive to the toxin (Khan et al., 1997). The screen of the present invention is capable of identifying genes involved directly or indirectly in the increased generation of ROS (loss-of-function mutants), as well as those which protect the cell from oxidation (gain-of-function mutants). Since DA itself may contribute to DA neurotoxicity (see below), mutations within the DA synthesizing (e.g., TH, AAAD), DA metabolizing (e.g., monoamine oxidase), and vesicle sequestration (e.g., VMAT, Vacuole $H^+$-ATPase [V-ATPase]) pathways are contemplated (Table 1) (Miller et al., 1999). Novel targets that would normally induce neuronal degeneration, independent of oxidative pathways and those involved in DA metabolism and sequestration, will also be identified by the screening methods described here.

If DA-ergic neuronal degeneration is dependent on the cell death or a necrotic pathway, then mutants within these pathways will also be identified by the present screening methods. Recent investigations suggest both neurotoxins may rely on products of programmed cell death pathways (see below). 6-OHDA causes shrinkage of DAergic cells, nuclear condensation and DNA fragmentation (i.e., apoptotic characteristics) in vitro, while $MPP^+$ does not induce these events (Choi et al., 1999). Morphological and biochemical correlates of $MPP^+$ toxicity in vitro are more consistent with necrosis rather than apoptosis displaying mitochondrial swelling and scattered heterochromatin (Choi et al., 1999). Interestingly, the anti-apoptotic protooncogenes in the Bcl-2 class can protect against both $MPP^+$ and 6-OHDA toxicity in vitro and in vivo, suggesting overlap between the two degradation pathways (Offen et al., 1998; Oh, et al., 1998). Apoptosis and necrotic death are both well-defined events in *C. elegans*, with apoptosis causing cytoplasmic shrinkage, mitochondria distortion, and rapid phagocytosis, while necrosis produces vacuoles, cell swelling, and membrane whorls (Baffi et al., 1999; Robertson and Thomson, 1982; Hall et al., 1997). Presently, little is known about the genes involved in the necrotic pathway, and considering that necrosis can follow neuronal insult independent of activation of the apoptotic pathway, novel genes involved in necrosis will likely be identified (Roy and Sapolsky, 1999).

Additionally, the present inventors envision using the *C. elegans* model described here to study the effects of these and other neurotoxins on DA neuronal degradation in assays independent of the genetic screens.

The inventors also contemplate using the existing wealth of *C. elegans* mutants (see for example mutants listed at http://www.elegans.swmed.edu/). For example, PD may be the result of excess DA in the cytoplasm due to the weakening of the ion gradients required for DA sequestration in vesicles. To determine if endogenous DA levels play a role in toxin-mediated neural degeneration, the inventors contemplate crossing the reporter line $P_{CeDAT}$::GFP to worm lines deficient in DA synthesis such as the TH (cat-2) or AAAD (bas-1) null mutants and test for sensitivity to 6-OHDA. There is also evidence that the endogenous VMAT levels may predict the sensitivity of the DA neurons to the toxins: the lower the amount of VMAT, greater the level of DA in the cytoplasm and therefore the greater the likelihood of neural degeneration (Miller et al., 1999). It is contemplated that this possibility will be tested by crossing the GFP reporter line into the VMAT null strain (cat-1) followed by screening for toxin induced neurodegeneration. It is also contemplated that reserpine an agent which blocks VMAT and inhibits DA vesicular storage, which causes a reduction in intracellular DA both in humans and worms), will be applied to WT worms prior to toxin exposure to determine the role of VMAT on neurotoxicity (Duerr et al., 1999; Sulston et al., 1975; Miller et al., 1999).

Cell Death. Additionally the inventors contemplate using the *C. elegans* model to explore genes involved in cell death. *C. elegans* was the first organism in which factors regulating cell death were identified on a genetic level. Mutants in these genes are available for evaluating their roles in DA neurodegeneration (Hengartner, 1997). For example, CED-3 is a member of the ICE-family of cysteine proteases or caspases, which are known to function in both nematode and mammalian apoptosis. CED-3 activity is required for programmed cell death and a ced-3 (lof) mutation blocks all programmed cell death in the nematode (Ellis and Horvitz, 1986). CED-4 is required for CED-3 activation. CED-9 is homologous to mammalian Bcl-2 and negatively regulates CED-3 through interactions with CED-4. Gain-of-function mutations in ced-9 also blocks apoptosis (Hengartner et al., 1992). The present inventors contemplate crossing the $P_{CeDAT}$::GFP line into the ced mutants to directly test if apoptosis is involved in 6-OHDA or $MPP^+$ neurotoxicity.

The inventors also contemplate that the CeDAT-directed screens will yield molecular insights into presynaptic DAT regulation and DA neurodegeneration. Due to the high similarity between the human and worm nervous systems at the molecular level, the molecules identified by these screens are envisioned to be of general relevance.

\*\*\*\*\*\*\*\*\*\*\*\*\*\*\*\*\*\*\*\*\*\*\*\*

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Baffi, Palkovits, Castillo, Mezey, Nikodem, "Differential expression of tyrosine hydroxylase in catecholaminergic neurons of neonatal wild-type and Nurr1-deficient mice," *Neuroscience*, 93: 631-642, 1999.

Bargmann, "Neurobiology of the *Caenorhabditis elegans* genome," *Science*, 282: 2028-2033, 1998.

BLAST search performed at WormBase using the WormPep Version 18 at http://www.wormbase.org/perl/ace/elegans/searches/blast Brenner, "The genetics of *Caenorhabditis elegans*," *Genetics*, 77: 71-94, 1974.

*C. elegans* Sequencing Consortium. Genome Sequence of the Nematode *C. elegans*: A platform for investigating biology, *Science*, 282: 2012-2018, 1998.

*Caenorhabditis elegans*, www.elegans.swmed.edu/

Castillo, Baffi, Palkovits, Goldstein, Kopin, Witta, Magnuson, Nikodem, "Dopamine biosynthesis is selectively abolished in substantia nigra/ventral tegmental area but not in hypothalamic neurons in mice with targeted disruption of the Nurr1 gene," 11: 36-46, 1998.

Chalfie, Tu, Euskirchen, Ward, Prasher, "Green fluorescent protein as a marker for gene expression," *Science*, 263: 802-805, 1994.

Chen N, Reith, *Eur J Pharmacol*, Sep. 29; 4005(1-3): 329-339, 2000.

Choi, Yoon, Oh, Choi, O'Malley, Oh, "Two distinct mechanisms are involved in 6-hydroxydopamine- and MPP+-induced dopaminergic neuronal cell death: role of caspases, ROS, and JNK," *J. Neurosci. Res.*, 57: 86-94, 1999.

Cohen and Heikkila, "The generation of hydrogen peroxide, superoxide radical, and hydroxyl radical by 6-hydroxydopamine, dialuric acid, and related cytotoxic agents," *J. Biol. Chem.*, 249: 2447-2452, 1974.

Duerr, Frisby, Gaskin, Duke, Asermely, Huddleston, Eiden, Rand, "The cat-1 gene of *Caenorhabditis elegans* encodes a vesicular monoamine transporter required for specific monoamine-dependent behaviors," *J. Neuroscience*, 9: 72-84, 1999. Ellis and Horvitz, "Genetic control of programmed cell death in the nematode *C. elegans*," *Cell*, 44: 817-829, 1986.

Emmons, Klass, Hirsh, "Analysis of the constancy of DNA sequences during development and evolution of the nematode *Caenorhabditis elegans*," *Proc. Natl. Acad. Sci. USA* 76: 1333-1337, 1979.

Fradkov, Chen, Ding, Barsova, Matz, Lukyanov, "A novel fluorescent protein from Discosoma coral and its mutants possesses a unique far-red fluorescence," *FEBS Lett*, 479 (3): 127-30, 2000.

Gainetdinov, Jones, Fumagalli, Wightman, Caron, Re-evaluation of the role of the dopamine transporter in dopamine system homeostasis, *Brain Res. Rev.*, 26: 148-153, 1998.

GenBank accession Number AF115382.

Giros and Caron, "Molecular characterization of the dopamine transporter," *Trends Pharm. Sci.*, 14: 43-49, 1993.

Giros, El Mstikawy, Godinot, Zheng, Han, Yang-Feng, Caron, "Cloning, pharmacological characterization, and chromosome assignment of the human dopamine transporter," *Mol. Pharm.*, 42: 383-390, 1992.

Giros, Jaber, Jones, Wightman, "Hyperlocomotion and indifference to cocaine and amphetamine in mice lacking the dopamine transporter," *Nature*, 379: 606-612, 1996.

Glinka, Gassen, Youdim, "Mechanism of action of 6-hydroxydopamine neurotoxicity," *J. Neural. Transm. Suppl.*, 50: 55-66, 1997.

Graham, Tiffany, Bell, Gutknecht, "Autooxidation versus covalent binding of quinones as the mechanism of toxicity of dopamine, 6-hydroxydopamine, related compounds toward C1300 neuroblastoma cells in vitro," *Mol. Pharmacol.*, 14: 644-653, 1978.

Hall, Gu, Garcia-Anoveros, Gong, Chalfie, Driscoll, "Neuropathology of degenerative cell death in *Caenorhabditis elegans*," *J. Neuroscience*, 17: 1033-1045, 1997.

Hengartner, "Cell death," In: *C. elegans II*, Riddle, Blumenthal, Meyer, Priess (Eds), New York: Cold Spring Harbor Laboratory Press; 383-415, 1997.

Hengartner, Ellis, Horvitz, "*Caenorhabditis elegans* gene ced-9 protects cells from programmed cell death," *Nature*, 356: 494-499, 1992.

Hope laboratory worm pages. URL: http://bgypc086.leeds.ac.uk/

Javitch, D'Amato, Strittmatter, Snyder, "Parkinsonism-inducing neurotoxin, N-methyl-4-phenyl-1,2,3,6-tetrahydropyridine: uptake of the metabolite N-methyl-4-pheynylpyridine by dopamine neurons explains selective toxicity," *Proc. Nat. Acad. Sci. USA*, 82: 2173-2177, 1985.

Jayanthi, Apparsundaram, Malone, Ward, Miller, Eppler, Blakely, "The *Caenorhabditis elegans* gene T23G5.5 encodes an antidepressant- and cocaine-sensitive dopamine transporter," *Mol. Pharmacol.*, 54: 601-609, 1998.

Jenner, "Oxidative mechanisms in nigral cell death in Parkinson's disease," *Mov. Disord.*, 13: 24-34, 1998.

Johnsen and Baillie, "Mutation," In: *C. elegans II*, Riddle, Blumenthal, Meyer, Priess (Eds.), New York: Cold Spring Harbor Press; 79-95, 1997.

Khan, Filiano, King, Przedborski, "Is Parkinson's disease (PD) an extra-mitochondrial disorder?" *Neurology*, 48: A201, 1997.

Kitayama, Shimada, Uhl, "Parkinsonism-inducing neurotoxin MPP+: uptake and toxicity in nornneuronal COS cells expressing dopamine transporter cDNA," *Ann. Neurol.*, 32: 109-111, 1992.

Kopin, "Features of the dopaminergic neurotoxin MPTP," *Acad Sci*, 648: 96-104, 1992.

Le, Conneely, He, Jankovic, Appel, "Reduced Nurr1 expression increases the vulnerability of mesencephalic dopamine neurons to MPTP-induced injury," *J. Neuroscience*, 73(5): 2218-2221, 1999.

Lewis and Fleming, "Basic culture methods in *Caenorhabditis elegans*: modern biological analysis of an organsism, *Methods Cell Biol*, 48: 3-29, 1995.

Lints and Emmons, "Genetic Analysis of Dopaminergic Neurons in the Nematode *Caenorhabditis elegans*," In: *Development of Dopaminergic Neurons*, di Porzio, Pernas-Alonso, Perrone-Capano (Eds.), Austin, Tex., R.G. Landes Company, 175-190, 1999.

Lints and Emmons, "Patterning of dopaminergic neurotransmitter identity among *Caenorhabditis elegans* ray sensory neurons by a TGFβ family signaling pathway and a Hox gene," *Development*, 126: 5819-5831, 1999.

Liu and Sternberg, "Sensory regulation of male mating behavior in *Caenorhabditis elegans*, *Neuron*, 14: 1-20, 1995.

Loer and Kenyon, "Serotonin-deficient mutants and male mating behavior in the nematode *Caenorhabditis elegans*," *J. Neuroscience*, 13: 5407-5417, 1993.

Lotharius, Dugan, O'Malley, "Distinct mechanisms underlie neurotoxin-mediated cell death in cultured dopaminergic neurons," *J. Neuroscience*, 19: 1284-1293, 1999.

Mello and Fire, "DNA transformation in *Caenorhabiditis elegans*: modern biological analysis of an organsism," Epstein and Shakes, (Eds.), *Methods Cell Biol*, 48: 451-482, (Chapter 19), 1995.

Mello and Fire, "DNA transformation in *Caenorhabiditis elegans*: modern biological analysis of an organsism," Epstein and Shakes, (Eds.), *Academic Press*, 1995.

Mello, Kramer, Stinchcomb, Ambros, "Efficient gene transfer in *C. elegans*: Extrachromosomal maintenance and integration of transforming sequences," *EMBO J.*, 10, 3959-3970, 1991.

Kramer, French, Park, Lohnson, "The *Caenorhabditis elegans* rol-6 gene, which interats with the sqt-1 collagen gene to determine organismal morphology, encodes a collagen," *Mol. Cell. Biol.*, 10: 2081-2090, 1990.

Miller, Desai, Hardin, Piston, Patterson, Fleenor, Xu, Fire, "Two-color GFP expression for *C. elegans*," *Biotechniques*, 26: 914-921, 1999a.

Miller, Gainetdinov, Levey, Caron, "Dopamine transporters and neuronal injury," *Trends Pharm. Sci.*, 20(10): 424-429, 1999b.

Nass, Duerr, Rand, Miller, Blakely, "6-OHDA sensitivity of dopaminergic neurons in *C. elegans*: role of the dopamine transporter and cell death pathways," *Society Neuroscience*, Abstract: 2000.

Nirenberg, Chan, Vaughan, Uhl, Kuhar, Pickely, "Immunogold localization of the dopamine transporter: an ultrastructural study of the rat vetral tegmental area," *J. Neuroscience*, 17: 5255-5262, 1997.

Offen, Beart, Cheung, Pascoe, Hochman, Gorodin, Melamed, Bernard, Bernard, "Transgenic mice expressing human Bcl-2 in their neurons are resistant to 6-hydroxydopamine and 1-methyl-4-phenyl-1,2,3,6-tetrahydropyridine neurotoxicity," *Proc. Natl. Acad. USA*, 95: 5789-5794, 1998.

Oh, Choi, Kim, Seo, O'Malley, Oh, "Overexpression of HA-Bax but not Bcl-2 or Bcl-XL attenuates 6-hydroxydopamine-induced neuronal apoptosis," *Exp. Neurol.*, 154: 193-198, 1998.

Pickel, Nirenberg, Milner, "Ultrastructual view of central catecholaminergic transmission: immunocytochemical localization of synthesizing enzymes, transporters, and receptors," *J. Neurocytology*, 25: 843-856, 1996.

Pifl, Giros, Caron, "Dopamine transporter expression confers cytotoxicity to low doses of the Parkinsonism-inducing neurotoxin 1-methyl-4-phenylpyridinium," *J. Neuroscience*, 13(10): 4246-4253, 1993.

Riddle, Blumenthal, Meyer, Priess, "Introduction to *C. elegans*," In: *C. elegans II*, New York: Cold Spring Harbor Laboratory Press, 1-22, 1997.

Robertson and Thomson, "Morphology of programmed cell death in the ventral nerve cord of *Caenorhabditis elegans*," *J. Embryol. Exp. Morphol.*, 67: 89-100, 1982.

Rongo, Whitfield, Rodal, Kim, Kaplan, "LIN-10 is a shared component of the polarized protein localization pathways in neurons and epithelia," *Cell*, 94: 751-759, 1998.

Roy and Sapolsky, "Neuronal apoptosis in acute necrotic insults: why is this subject such a mess?" *Trends in Neuroscience*, 22; 419-422, 1999.

Sachs and Jonsson, "Mechanism of action of 6-hydroxydopamine," *Biochem. Pharmacol*, 24: 1-8, 1975.

Sawin, Ranganathan, Horvitz, "*C. elegans* locomotory rate is modulated by the environment through a dopaminergic pathway and by experience through a serotonergic pathway," *Neuron*, 26: 619-631, 2000.

Stinchcomb, Shaw, Carr, Hirsch, "Extrachromosomal DNA transformation of *Caenorhabditis elegans*, *Mol. Cell Bio.*, 5: 3484-3496, 1985.

Sulston and Horvitz, "Post-embryonic cell lineages of the nematode, *Caenorhabditis elegans*, *Dev. Biol.*, 56: 110-156, 1977.

Sulston, Dew, Brenner, "Dopaminergic neurons in the nematode *Caenorhabditis elegans*," *J. Comp. Neurol.*, 163: 215-226, 1975.

Sulston, Du, Thomas, Wilson, Hillier, Staden, Halloran, Green, Thierry-Mieg, Qiu, Dear, Coulson, Craxton, Durbin, Berks, Metzstein, Hawkins, Ainscough, Waterson, "The *C. elegans* genome sequencing project: a beginning," *Nature*, 356: 37-41, 1992.

Sulston and Hodgkin, "Methods," In: *The nematode Caenorhabditis elegans*, Wood and the Community of *C. elegans* Researchers (eds.), Cold Spring Harbor Laboratory, Cold Spring Harbor, N.Y., 587-606, 1988.

White, Southgate, Thompson, Brenner, "The structure of the nervous system of the nematode *Caenorhabditis elegans*," *Philos. Trans. R. Soc. Lond. B. Biol. Sci.*, 314: 1-340, 1986.

Wood, "Introduction to *C. elegans* Biology," In: *The nematode C. elegans*, Wood (ed.), New York: Cold Spring Harbor Laboratory Press; 1-16, 1988.

Yahr and Bergmann, In: *Advances in Neurology: Parkinson's Disease*, New York: Raven Press, 1986.

What is claimed is:

1. A method of screening for substances that affect neuronal viability comprising:
   a) providing a recombinant *Caenorhabditis elegans*, the genome of which comprises a transgene that encodes a detectable marker and is under the control of a promoter, wherein said detectable marker is expressed in a neuronal cell of said recombinant *C. elegans*;
   b) exposing said *C. elegans* to a candidate substance; and
   c) detecting a change in the expression of the detectable marker relative to the expression of the detectable marker before said exposing;
   wherein a change in the expression of the detectable marker corresponds to a change in the viability of the neuron.

2. The method of claim 1, further comprising detecting the expression of the detectable marker in the neuronal cell in the absence of said candidate substance.

3. The method of claim 1, wherein said substance is a neurotoxic substance.

4. The method of claim 3, wherein the neurotoxic substance is 6-hydroxydopamine, 1-methyl-4-phenyl-1,2,3,6-tetrahydropyridine, or 5,7, di-hydroxy tryptamine.

5. The method of claim 3, wherein the neurotoxic substance is 6-hydroxydopamine.

6. The method of claim 3, wherein the neurotoxic substance is a generator of free radical species.

7. The method of claim 1, further comprising the step of exposing said *C. elegans* to a known neurotoxin prior to step b).

8. The method of claim 1, further comprising the step of exposing said *C. elegans* to a known neurotoxin after step b).

9. The method of claim 1, wherein the change in detectable marker expression can be an increase in the detectable marker.

10. The method of claim 1, wherein the change in detectable marker expression can be a decrease in the detectable marker.

11. The method of claim 1, wherein the detectable marker is further defined as a marker that can be visually detected.

12. The method of claim 1, wherein the detectable marker is further defined as a marker that can be spectroscopically detected.

13. The method of claim 12, wherein the detectable marker is a green fluorescent protein.

14. The method of claim 12, wherein the detectable marker is a yellow fluorescent protein.

15. The method of claim 12, wherein the detectable marker is a blue fluorescent protein.

16. The method of claim 12, wherein the detectable marker is a red fluorescent protein.

17. The method of claim 1, wherein the detectable marker is β-galactosidase.

18. The method of claim 1, wherein the detectable marker is an antigenic polypeptide.

19. The method of claim 1, wherein the neuronal cell comprises a dopaminergic neuron.

20. The method of claim 1, wherein the neuronal cell comprises a cholinergic neuron.

21. The method of claim 1, wherein the neuronal cell comprises a GABA-ergic neuron.

22. The method of claim 1, wherein the neuronal cell comprises a glycinergic neuron.

23. The method of claim 1, wherein the neuronal cell comprises a serotonergic neuron.

24. The method of claim 1, wherein the neuronal cell comprises a glutamatergic neuron.

25. The method of claim 1, wherein the neuronal cell comprises a peptidergic neuron.

* * * * *